United States Patent
Rebacz et al.

(10) Patent No.: US 12,201,759 B2
(45) Date of Patent: Jan. 21, 2025

(54) CONDUCTIVITY CONTROL SYSTEMS

(71) Applicant: Fresenius Medical Care Holdings, Inc., Waltham, MA (US)

(72) Inventors: Natalie Rebacz, Waltham, MA (US); Kerissa Adams, Norman, OK (US); Stephen A. Merchant, Waltham, MA (US); Mary Hoover, Waltham, MA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 413 days.

(21) Appl. No.: 17/625,124

(22) PCT Filed: Aug. 3, 2020

(86) PCT No.: PCT/US2020/044751
§ 371 (c)(1),
(2) Date: Jan. 6, 2022

(87) PCT Pub. No.: WO2021/026073
PCT Pub. Date: Feb. 11, 2021

(65) Prior Publication Data
US 2022/0265910 A1    Aug. 25, 2022

Related U.S. Application Data

(60) Provisional application No. 62/882,733, filed on Aug. 5, 2019.

(51) Int. Cl.
*A61M 1/16* (2006.01)
*A61M 1/14* (2006.01)
*B01D 61/24* (2006.01)

(52) U.S. Cl.
CPC ........ *A61M 1/1696* (2013.01); *A61M 1/1524* (2022.05); *A61M 1/154* (2022.05);
(Continued)

(58) Field of Classification Search
CPC .. A61M 1/1696; A61M 1/1524; A61M 1/154; A61M 1/155; A61M 1/1565;
(Continued)

(56) References Cited

U.S. PATENT DOCUMENTS 2,530,581 A  11/1950  Markis et al.
3,973,683 A   8/1976  Keller
(Continued)

FOREIGN PATENT DOCUMENTS

CN   205368031 U  *  7/2016
EP       1509261      3/2005
(Continued)

OTHER PUBLICATIONS

English translation of patent publication CN-205368031-U, published Jul. 6, 2016. (Year: 2016).*

(Continued)

*Primary Examiner* — Joseph W Drodge
(74) *Attorney, Agent, or Firm* — Fish & Richardson P.C.

(57) ABSTRACT

A dialysis system has a module with a dialyzer configured to remove one or more substances from a dialysis solution as it passes through a dialyzer. The module has a fluid line, a sorbent cartridge, and a sodium control system adapted to actively alter a sodium concentration of dialysis solution passing through the fluid line as the dialysis solution exits the sorbent cartridge. The sodium control system has a conductivity sensor that sends a signal indicating the conductivity of the dialysis solution as the dialysis solution exits the sorbent cartridge, the conductivity meter being in communication with the sodium control system, a processor configured to receive the signal from the conductivity sensor, compare the conductivity signal to a threshold value lower than a prescription value, and cause the sodium
(Continued)

control system to stop actively altering the sodium concentration if the signal is greater than the threshold value.

19 Claims, 31 Drawing Sheets

(52) U.S. Cl.
CPC .......... *A61M 1/155* (2022.05); *A61M 1/1565* (2022.05); *A61M 1/1605* (2014.02); *A61M 1/1561* (2022.05); *A61M 2205/3317* (2013.01)

(58) Field of Classification Search
CPC .............. A61M 1/1605; A61M 1/1561; A61M 2205/3317; A61M 1/1656; A61M 1/1609; A61M 2205/33; B01D 61/24; B01D 61/243; B01D 61/30; B01D 61/32; B01D 2311/2626
See application file for complete search history.

(56) References Cited

U.S. PATENT DOCUMENTS

| | | | |
|---|---|---|---|
| 4,001,556 | A | 1/1977 | Folchi et al. |
| 4,229,136 | A | 10/1980 | Panissidi |
| 4,274,802 | A | 6/1981 | Inaba et al. |
| 4,363,585 | A | 12/1982 | Keller et al. |
| 4,687,941 | A | 8/1987 | Laserberg et al. |
| 5,111,997 | A | 5/1992 | Ikuta et al. |
| 5,540,668 | A | 7/1996 | Wilson, Jr. et al. |
| 5,622,468 | A | 4/1997 | Viollet |
| 6,939,111 | B2 | 9/2005 | Huitt et al. |
| 7,162,884 | B2 | 1/2007 | Alles |
| 7,216,672 | B1 | 5/2007 | Chen |
| 8,555,926 | B2 | 10/2013 | MacDuff et al. |
| 9,827,361 | B2 | 11/2017 | Pudil et al. |
| 9,931,447 | B2 | 4/2018 | Layser et al. |
| 10,058,694 | B2 | 8/2018 | Norris et al. |
| 11,000,638 | B2 * | 5/2021 | Gagel ................ A61M 1/165 |
| 11,085,552 | B2 | 8/2021 | Moss et al. |
| 2003/0098270 | A1 | 5/2003 | Thompson |
| 2004/0221904 | A1 | 11/2004 | Usher et al. |
| 2005/0274658 | A1 | 12/2005 | Rosenbaum et al. |
| 2007/0272311 | A1 | 11/2007 | Trocki et al. |
| 2008/0172006 | A1 | 7/2008 | Hicks |
| 2008/0214979 | A1 | 9/2008 | Brugger et al. |
| 2009/0127193 | A1 * | 5/2009 | Updyke .............. A61M 1/3472 |
| | | | 210/636 |
| 2010/0198129 | A1 | 8/2010 | Sternby et al. |
| 2010/0312174 | A1 | 12/2010 | Hoffman |
| 2011/0017665 | A1 * | 1/2011 | Updyke .................. A61M 1/28 |
| | | | 210/96.2 |
| 2012/0258545 | A1 * | 10/2012 | Ash ..................... A61M 1/1656 |
| | | | 210/85 |
| 2014/0088482 | A1 | 3/2014 | Schlaeper et al. |
| 2014/0097371 | A1 | 4/2014 | Huynh |
| 2015/0343127 | A1 | 12/2015 | Childers et al. |
| 2016/0008529 | A1 | 1/2016 | Hoffman |
| 2016/0239025 | A1 | 8/2016 | van Dder Merwe et al. |
| 2017/0106131 | A1 | 4/2017 | Hornig |
| 2017/0189598 | A1 | 7/2017 | Slade |
| 2017/0304516 | A1 * | 10/2017 | Burnes ................... B01D 61/32 |
| 2018/0021501 | A1 * | 1/2018 | Gerber ................... A61K 33/14 |
| | | | 604/28 |
| 2018/0229021 | A1 | 8/2018 | Donlon et al. |
| 2019/0134289 | A1 | 5/2019 | Pudil et al. |
| 2020/0030518 | A1 | 1/2020 | Brugger et al. |
| 2020/0033897 | A1 | 1/2020 | Jensen et al. |
| 2020/0041021 | A1 | 2/2020 | Moss et al. |
| 2020/0179674 | A1 | 6/2020 | Moss et al. |
| 2020/0271232 | A1 | 8/2020 | Nakagami et al. |
| 2021/0299340 | A1 | 9/2021 | Adams et al. |
| 2021/0341073 | A1 | 11/2021 | Moss et al. |

FOREIGN PATENT DOCUMENTS

| | | |
|---|---|---|
| EP | 2694127 | 2/2014 |
| GB | 2458572 | 9/2009 |
| WO | WO 2002/043859 | 6/2002 |
| WO | WO 2002/090671 | 11/2002 |
| WO | WO 2003/099355 | 12/2003 |
| WO | WO 2009/064984 | 5/2009 |
| WO | WO 2011/017215 | 2/2011 |

OTHER PUBLICATIONS

International Preliminary Report on Patentability in International Appln. No. PCT/US2019/042967, mailed Feb. 11, 2021, 7 pages.
International Preliminary Report on Patentability in International Appln. No. PCT/US2019/043023, mailed Feb. 11, 2021, 7 pages.
International Preliminary Report on Patentability in International Appln. No. PCT/US2019/044306, mailed Feb. 11, 2021, 8 pages.
International Preliminary Report on Patentability in International Appln. No. PCT/US2019/057775, mailed Jun. 17, 2021, 9 pages.
International Preliminary Report on Patentability in International Appln. No. PCT/US2020/044751, mailed Feb. 17, 2022, 11 pages.
International Search Report and Written Opinion in International Appln. No. PCT/US2019/042967, dated Oct. 8, 2019, 11 pages.
International Search Report and Written Opinion in International Appln. No. PCT/US2019/043023, dated Oct. 8, 2019, 9 pages.
International Search Report and Written Opinion in International Appln. No. PCT/US2019/044306, mailed Oct. 24, 2019, 13 pages.
International Search Report and Written Opinion in International Appln. No. PCT/US2019/057775, mailed Apr. 2, 2020, 17 pages.
International Search Report and Written Opinion in International Appln. No. PCT/US2020/044751, mailed Nov. 4, 2020, 18 pages.
Invitation to Pay Additional Fees in International Application No. PCT/US2019/057775, dated Feb. 11, 2020, 11 pages.

* cited by examiner

CONDUCTIVITY CONTROL SYSTEMS

TECHNICAL FIELD

This disclosure relates to fluid conditioning systems for generating and conditioning dialysis fluid utilized by dialysis machines to carry out dialysis treatments.

BACKGROUND

Dialysis is a treatment used to support a patient with insufficient renal function. The two principal dialysis methods include hemodialysis (HD) and peritoneal dialysis (PD). During HD, the patient's blood is passed through a dialyzer of a dialysis machine, while a dialysis solution (or, dialysate) is also passed through the dialyzer. A semi-permeable membrane in the dialyzer separates the blood from the dialysate and allows fluid exchanges to take place between the dialysate and the blood stream via diffusion, osmosis, and convective flow. These exchanges across the membrane result in the removal of waste products (e.g., such as solutes, like urea and creatinine) from the blood. These exchanges also regulate the levels of other substances (e.g., sodium and water) in the blood. In this way, the dialysis machine acts as an artificial kidney for cleansing the blood.

During peritoneal dialysis ("PD"), the patient's peritoneal cavity is periodically infused with dialysate. The membranous lining of the patient's peritoneum acts as a natural semi-permeable membrane that allows diffusion and osmosis exchanges to take place between the solution and the blood stream. These exchanges across the patient's peritoneum result in the removal of waste products (e.g., such as solutes, like urea and creatinine) from the blood and regulate the levels of other substances (e.g., sodium and water) in the blood.

SUMMARY

This disclosure relates to fluid conditioning systems for generating and conditioning dialysis fluid utilized by dialysis machines to carry out dialysis treatments. Described is a sorbent-based dialysis system that uses a sodium control system, including conductivity sensors, to control the level of sodium in the dialysis solution. During dialysis, the sodium concentration of the dialysate changes as the sorbent cartridge and the patient release additional sodium into the dialysate as it is recycled by passing through the sorbent cartridge and as it is in contact with the patient's blood. In previous systems, dialysate would be generated at the correct sodium level from the beginning of treatment. As treatment progressed, the sodium level was increased when it was too low by adding sodium chloride or decreased if too high by adding dilution water. A large volume of dilution water is used using this method.

As described herein, a dialysate generation machine generates dialysate that has a lower sodium concentration than is desired for a patient. This method ensures that the average sodium concentration of the dialysate for the overall treatment will be about equal to the desired dialysate concentration without having to add a large volume of dilution water and while decreasing the amount of sodium chloride that is used.

The systems and methods described herein can advantageously eliminate the high volume of water usage, expensive and noisy reverse osmosis equipment, and the need for a drain line that occur with many known dialysis systems and methods. Thus, the systems and methods described herein can enable a hemodialysis machine to be relatively easily modified for use in a home environment without requiring the installation of special plumbing or wiring in a patient's home. In addition, the systems and methods described herein can allow levels of sodium in the dialysis solution to be maintained within substantially the same physiological range as is achieved in single-pass hemodialysis. The treatment algorithms described for improved dialysate conductivity control utilizing sodium bicarbonate and dilution water addition provides a dialysis therapy that treats an estimated 80% of the patient population using a single machine configuration and prescription.

In one aspect, a dialysis system includes a module that is connected to a dialysis machine having a dialyzer configured to remove one or more substances from a dialysis solution as the dialysis solution passes through the dialyzer, the module including a fluid line in fluid communication with the dialyzer, a sorbent cartridge in fluid communication with the fluid line, and a sodium control system in fluid communication with the fluid line, the sodium control system being adapted to actively alter a sodium concentration of dialysis solution passing through the fluid line as the dialysis solution exits the sorbent cartridge. The sodium control system including a conductivity sensor that is adapted to send a signal indicating the conductivity of the dialysis solution as the dialysis solution exits the sorbent cartridge, the conductivity meter being in communication with the sodium control system, and a processor configured to receive the signal from the conductivity sensor, compare the conductivity signal to a threshold value lower than a prescription value, and cause the sodium control system to stop actively altering the sodium concentration if the signal is greater than the threshold value and adding dilution water to the solution exiting the sorbent cartridge if the signal is greater than the prescription value.

Embodiments may include one or more of the following features. A first container that stores sodium bicarbonate in communication with the fluid line. The sodium control system is configured to introduce the sodium bicarbonate into the fluid line via a first pump. Actively altering the sodium concentration includes introducing the sodium bicarbonate into the fluid line. A second container that stores a diluent in communication with the fluid line. The sodium control system is configured to introduce the diluent from the second container to the fluid line. The sodium control system is configured to introduce diluent to the fluid line when the processor indicates that the signal from the conductivity sensor is higher than the prescription value. The sorbent cartridge includes at least one layer of material capable of regenerating spent dialysis solution.

In one aspect, a dialysis system includes a dialysis machine and a module that is connected to a dialysis machine having a dialyzer configured to remove one or more substances from a dialysis solution as the dialysis solution passes through the dialyzer. The module including a fluid line in fluid communication with the dialyzer, a sorbent cartridge in fluid communication with the fluid line, and a sodium control system in fluid communication with the fluid line, the sodium control system being adapted to actively alter a sodium concentration of dialysis solution passing through the fluid line as the dialysis solution exits the sorbent cartridge. The sodium control system including a conductivity sensor that is adapted to send a signal indicating the conductivity of the dialysis solution as the dialysis solution exits the sorbent cartridge, the conductivity meter being in communication with the sodium control system, and a processor configured to receive the signal from the conductivity sensor, compare the conductivity signal to a threshold value lower than a prescription value, and cause the sodium control system to stop actively altering the sodium concentration if the signal is greater than the threshold value and adding dilution water to the solution exiting the sorbent cartridge if the signal is greater than the prescription value.

Embodiments may include one or more of the following features. The dialysis machine is a hemodialysis machine. A first container that stores sodium bicarbonate in communication with the fluid line. The sodium control system is configured to introduce the sodium bicarbonate into the fluid line via a first pump. Actively altering the sodium concentration includes introducing the sodium bicarbonate into the fluid line. A second container that stores a diluent in communication with the fluid line. The sodium control system is configured to introduce the diluent from the second container to the fluid line. Sodium control system is configured to introduce diluent to the fluid line when the processor indicates that the signal from the conductivity sensor is higher than the prescription value. The sorbent cartridge includes at least one layer of material capable of regenerating spent dialysis solution.

In one aspect, a method includes removing one or more substances from spent dialysis solution by passing the spent dialysis solution through a sorbent cartridge, receiving a signal from a conductivity sensor, comparing the conductivity signal to a threshold value lower than a prescription value, stopping altering the sodium concentration of solution exiting the sorbent cartridge when the signal is greater than the threshold value, and adding dilution water to the solution exiting the sorbent cartridge if the signal is greater than the prescription value. Embodiments may include passing the solution exiting the device through a dialysis machine.

Other aspects, features, and advantages will be apparent from the description, the drawings, and the claims.

DETAILED DESCRIPTION

Figure 1:
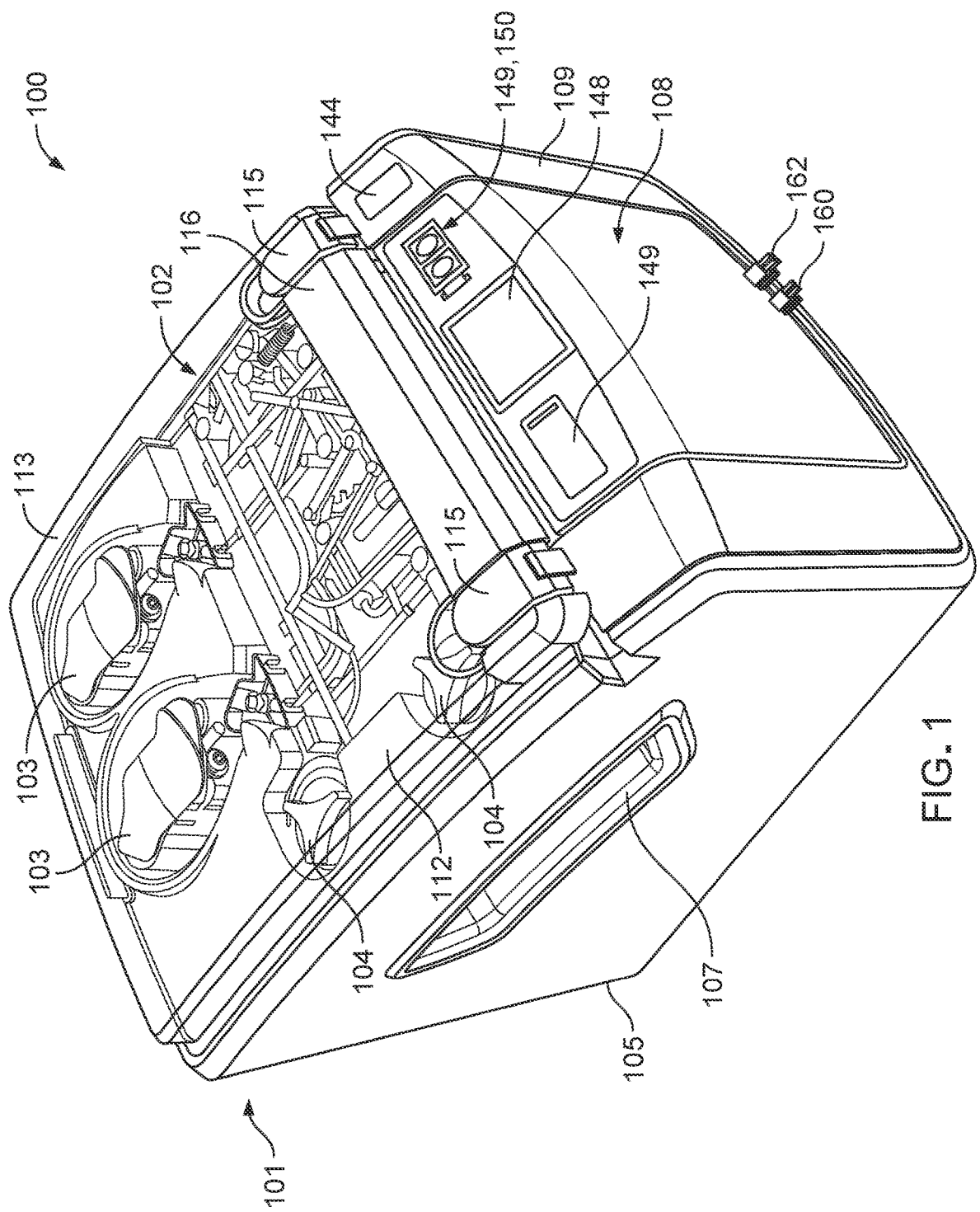
FIG. 1 is a perspective view of a fluid conditioning system that can cooperate with a dialysis system to carry out a fluid conditioning cycle that includes a dialysis treatment.
Figure 2:
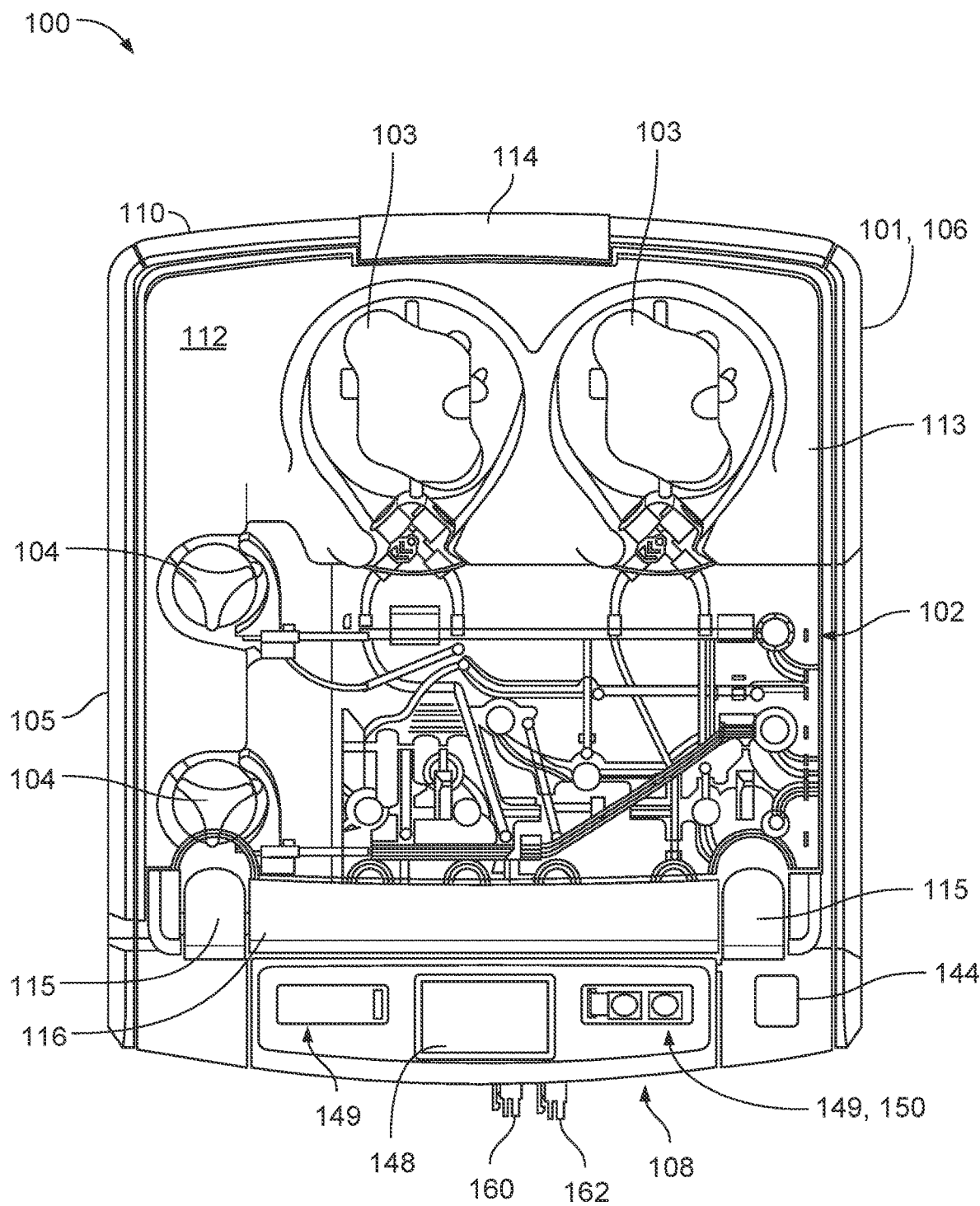
FIG. 2 is a top view of the fluid conditioning system of FIG. 1.
Figure 3:
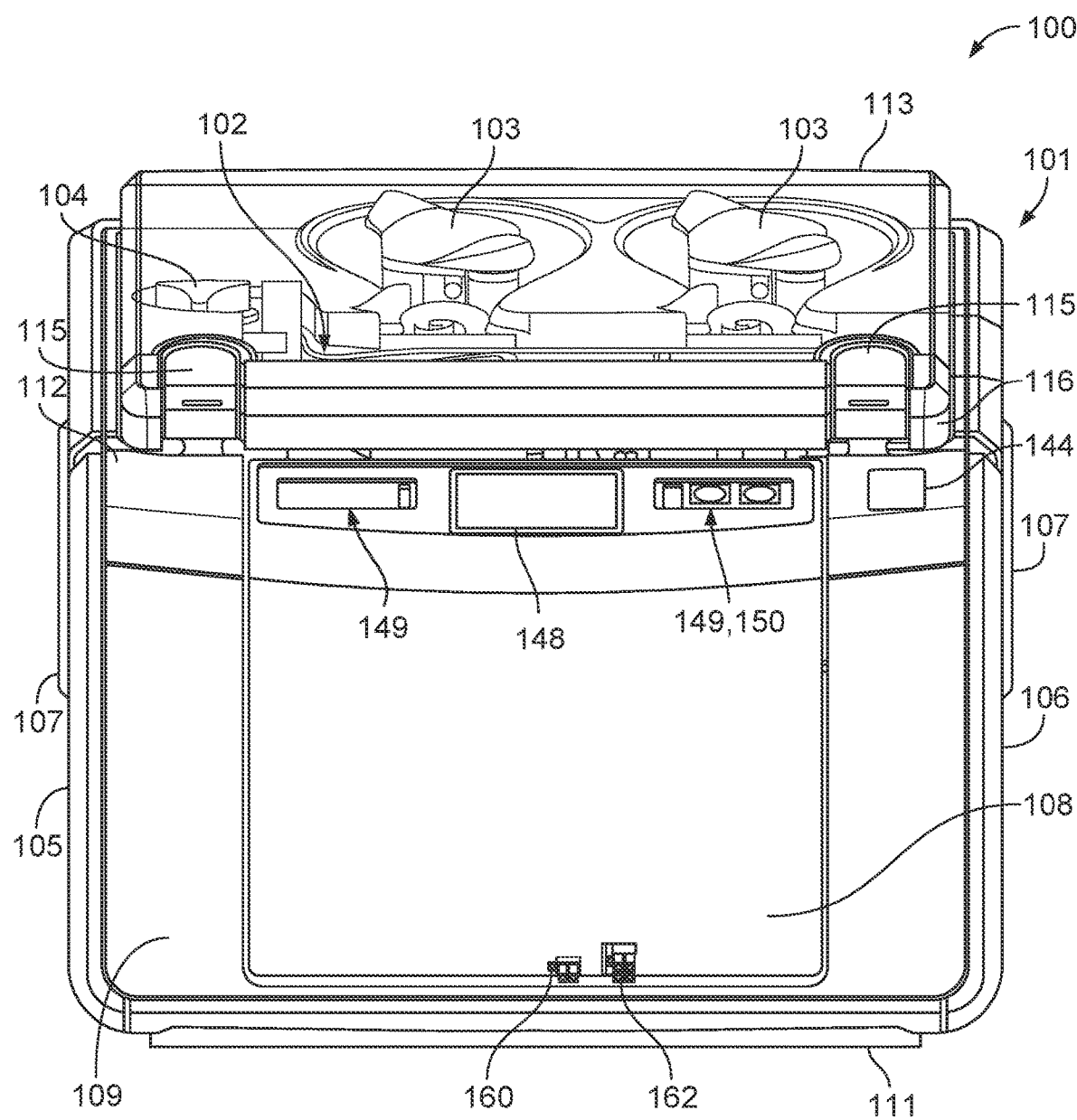
FIG. 3 is a front view of the fluid conditioning system of FIG. 1.
Figure 4:
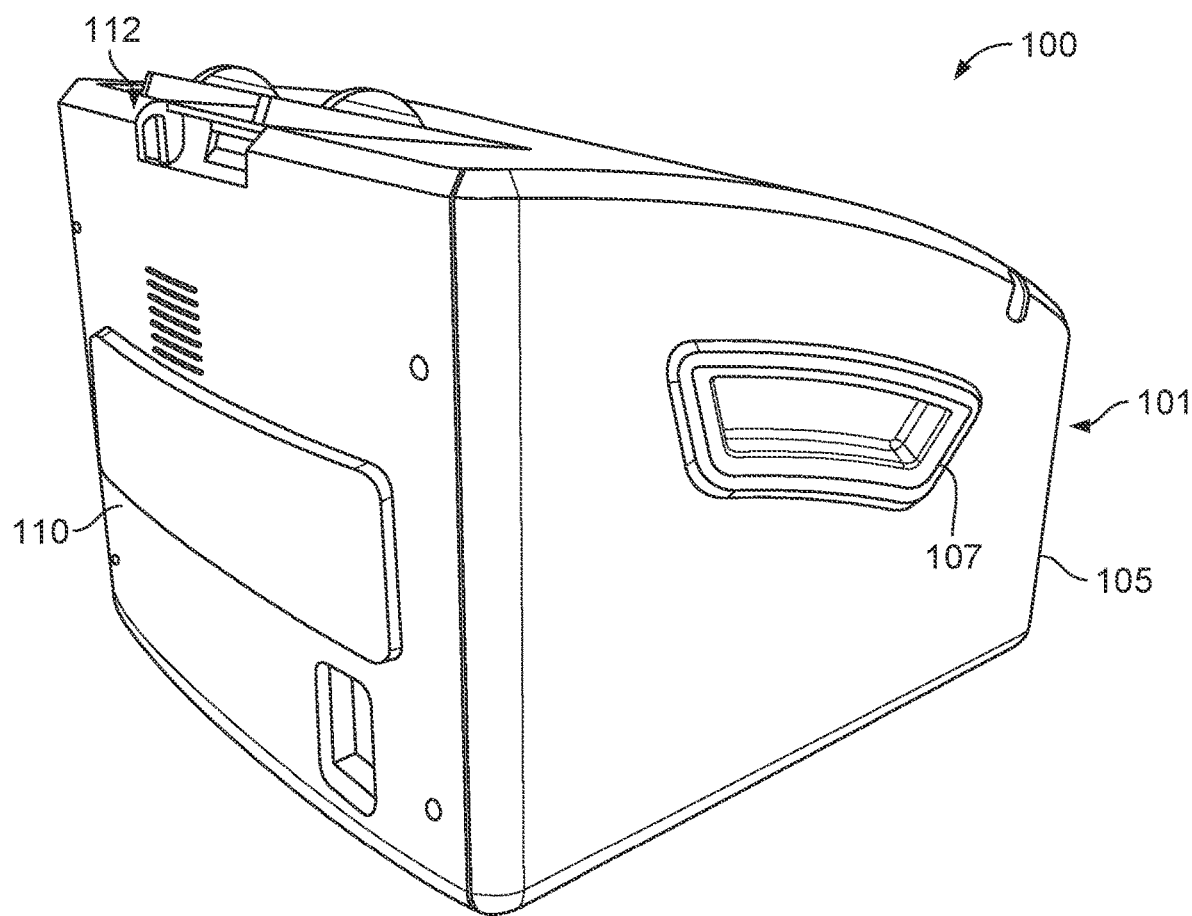
FIG. 4 is a rear view of the fluid conditioning system of FIG. 1.

Previous sodium-control systems for dialysis have used a dual-phase sodium regulation. This regulation is in accordance with a prescription guide, generally input by a user, and indicates what desired level of sodium concentration of the dialysate is desired when averaged over the treatment. During the first treatment phase, a sodium chloride solution is added to the dialysate to regulate its conductivity. The amount of sodium chloride added during a treatment can be significant. Then follows a second phase where the system compensates for excess sodium present above the desired prescription amount by adding dilution water. The amount of dilution water added during a treatment can be significant. Methods are described herein for regulating sodium content in dialysate while avoiding addition of excess sodium and of dilution water. In these methods, the sorbent cartridge used for filtering used dialysis solution in connection with a sodium control system in fluid communication regulates the sodium levels within the dialysis solution by controlling conductivity.

FIGS. 1-4 illustrate a fluid conditioning system 100 that can be operated to prepare conditioned dialysate for use in a dialysis system. For example, the fluid conditioning system 100 can be fluidly communicated with the dialysis system to deliver "fresh" (e.g., cleaned, conditioned) dialysate to the dialysis system, collect "spent" (e.g., contaminated, unconditioned) dialysate from the dialysis system, and regenerate (e.g., cleanse) and condition the spent dialysate in a continuous fluid flow loop to recycle the spent dialysate. Example dialysis systems with which the fluid conditioning system 100 can be fluidly communicated include hemodialysis (HD) systems, peritoneal dialysis (PD) systems, hemofiltration (HF), hemodiafiltration (HDF) and other related systems.

The fluid conditioning system 100 includes a housing 101 that contains or supports components of the fluid conditioning system 100, a fluid cassette 102 that includes multiple fluid lines defining various fluid pathways, two relatively high capacity pumps 103 that can circulate fluid within the fluid lines of the fluid cassette 102, and two relatively low capacity pumps 104 that can deliver (e.g., infuse) conditioning agents into the fluid circulating within the fluid lines of the fluid cassette 102. The fluid conditioning system 100 has a compact footprint that facilitates lifting and transport of the fluid conditioning system 100. For example, the fluid conditioning system 100 typically has a length of about 30 cm to about 50 cm, a width of about 30 cm to about 50 cm, a height of about 30 cm to about 50 cm, and a weight of about 15 kg to about 20 kg.

The housing 101 includes left and right side panels 105, 106, handles 107 positioned along the side panels 105, 106 for carrying the fluid conditioning system 100, a door assembly 108 that can be opened and closed to insert a heater bag, a front panel 109 to which the door assembly 108 is secured, rear and bottom panels 110, 111 that further enclose the interior components, an upper panel 112 that supports the fluid cassette 102 and the pumps 103, 104, and a cover 113 that protects the fluid cassette 102 and the pumps 103, 104. Example materials from which the exterior panels of the housing 101 may be made include plastics, such as acrylonitrile butadiene styrene (ABS) and polycarbonate blends, among others.

The cover 113 is typically made of ABS or polycarbonate and is transparent or translucent to allow visualization of the fluid cassette 102 and the pumps 103, 104. The cover 113 can be pivoted at a rear hinge 114 disposed along the upper panel 112 to open or close the cover 113. The upper panel 112 carries two latches 115 that can be closed upon a front edge 116 of the cover 113 to secure the cover 113 in a closed position. The latches 115 can also be pulled up and apart from the cover 113 to release the cover 113 from the closed position for accessing the fluid cassette 102 and the pumps 103, 104.

Figure 5:
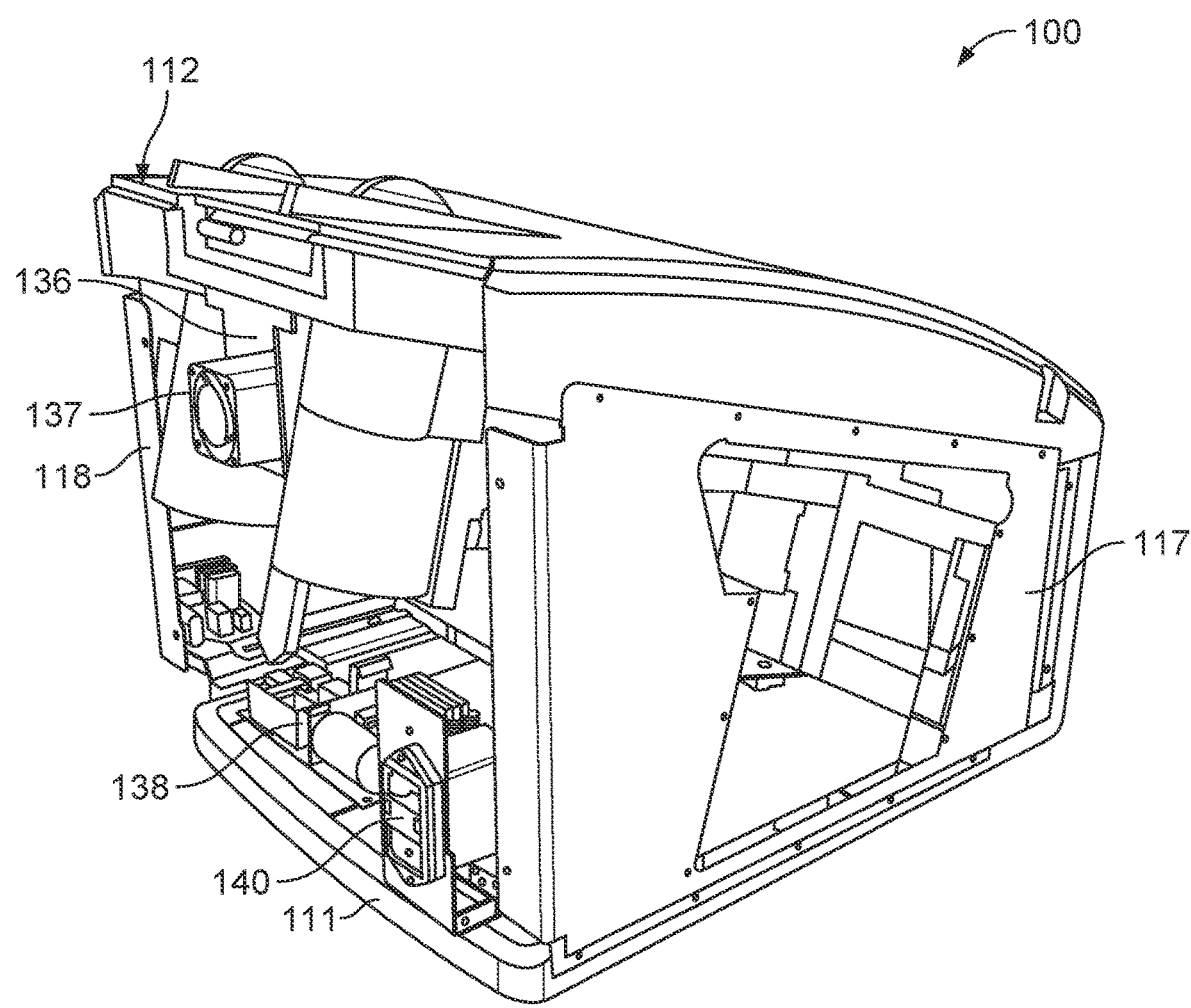
FIG. 5 is a rear view of the fluid conditioning system of FIG. 1, with certain exterior components omitted to expose certain interior components.

Referring to FIG. 5, the fluid conditioning system 100 also includes left and right side interior support frames 117, 118 to which the left side, right side, front, rear, bottom, and upper panels 105, 106, 109, 110, 111, 112 are attached. The interior support frames 117, 118 are typically formed from sheet metal.

Each pump 103, 104 is a peristaltic pump that includes multiple rollers positioned about the circumference of a rotatable frame (e.g., a motor) that carries a fluid line extending from the fluid cassette 102. As the rotatable frame is rotated, the rolling members apply pressure to the fluid line, thereby forcing fluid to flow through the fluid line.

Figure 6:
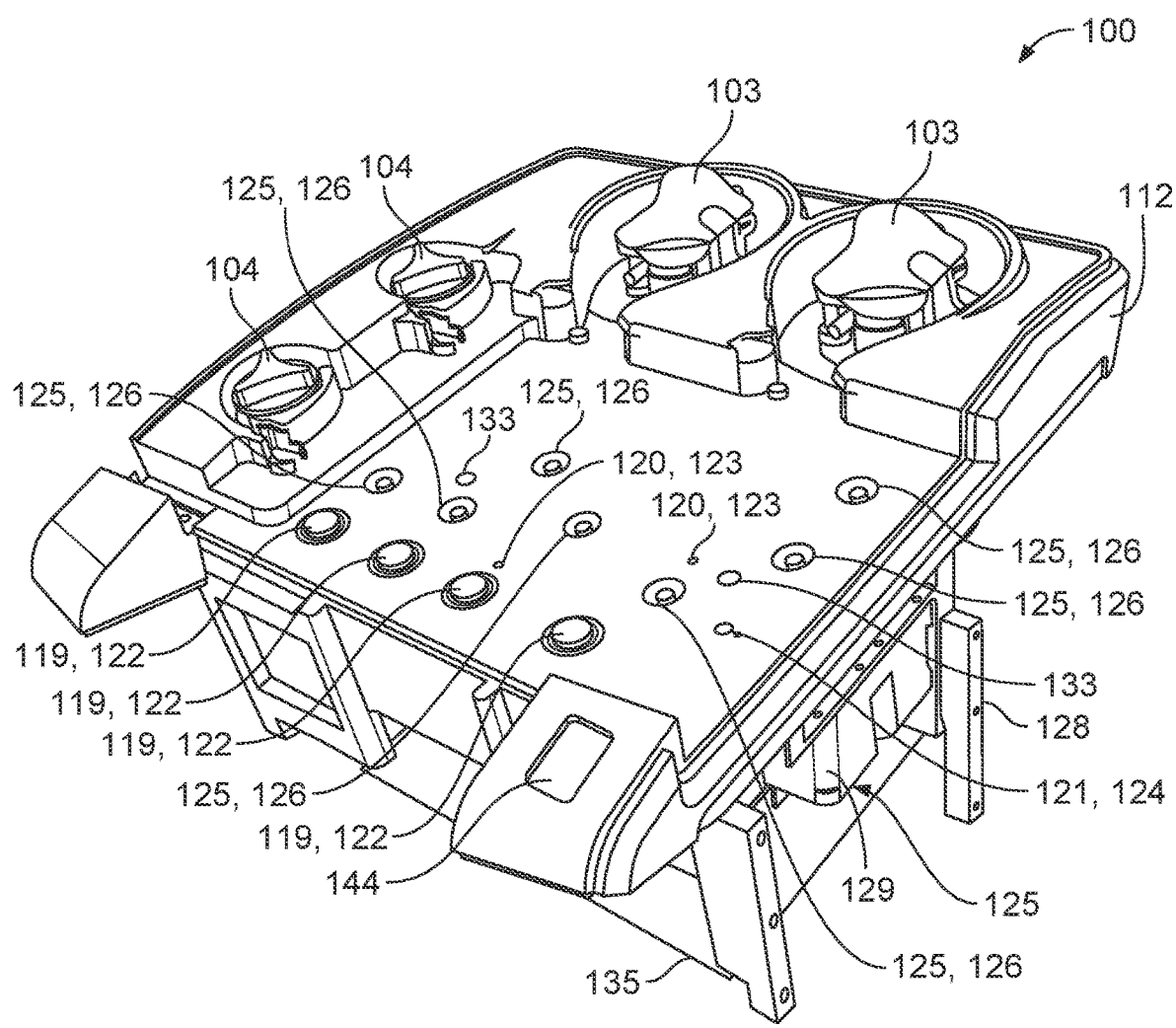
FIG. 6 is a perspective view of the fluid conditioning system of FIG. 1, with certain exterior components omitted to expose certain interior components.
Figure 7:
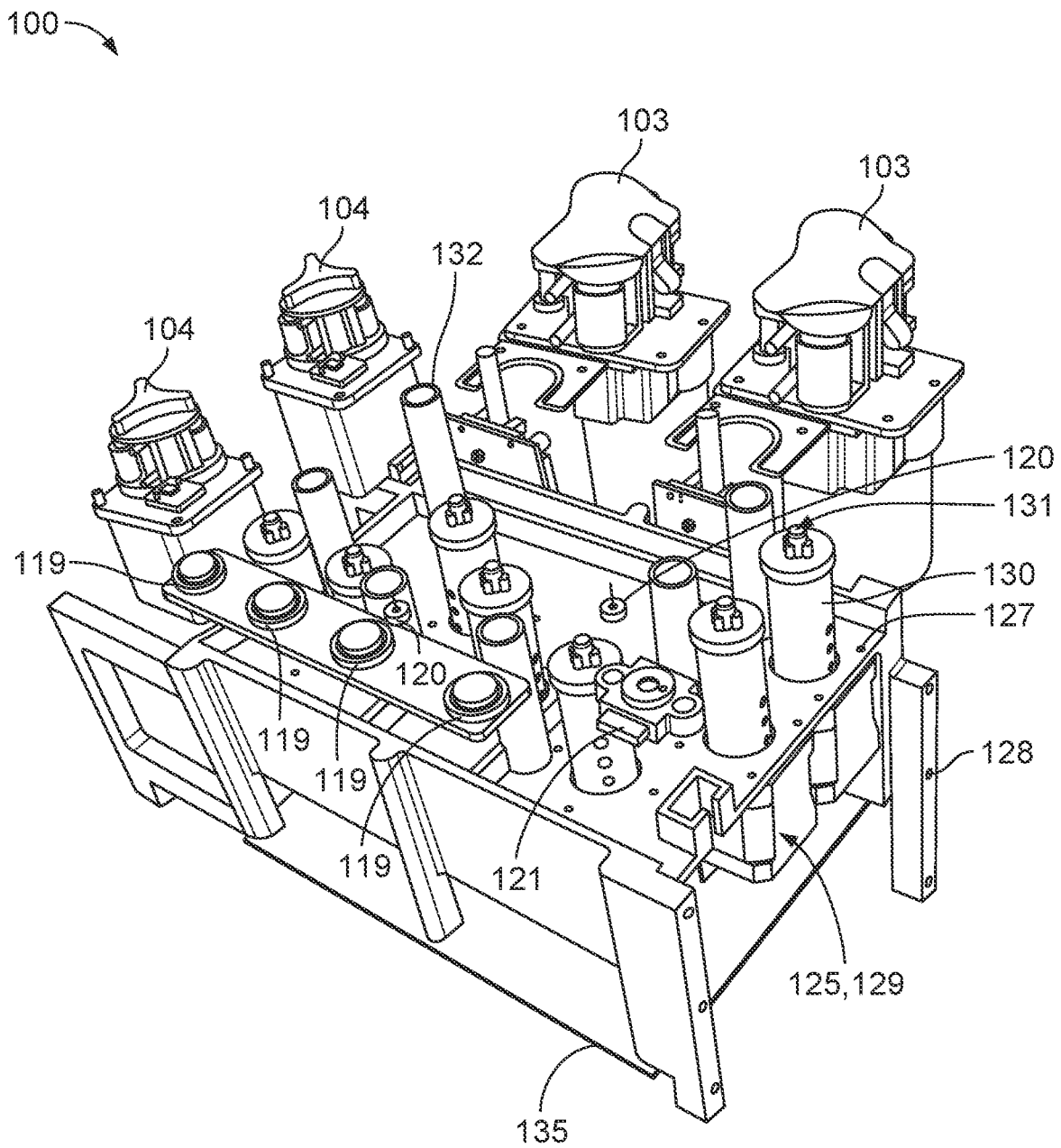
FIG. 7 is a perspective view of the fluid conditioning system of FIG. 1, with certain exterior components omitted to expose certain interior components.
Figure 8:
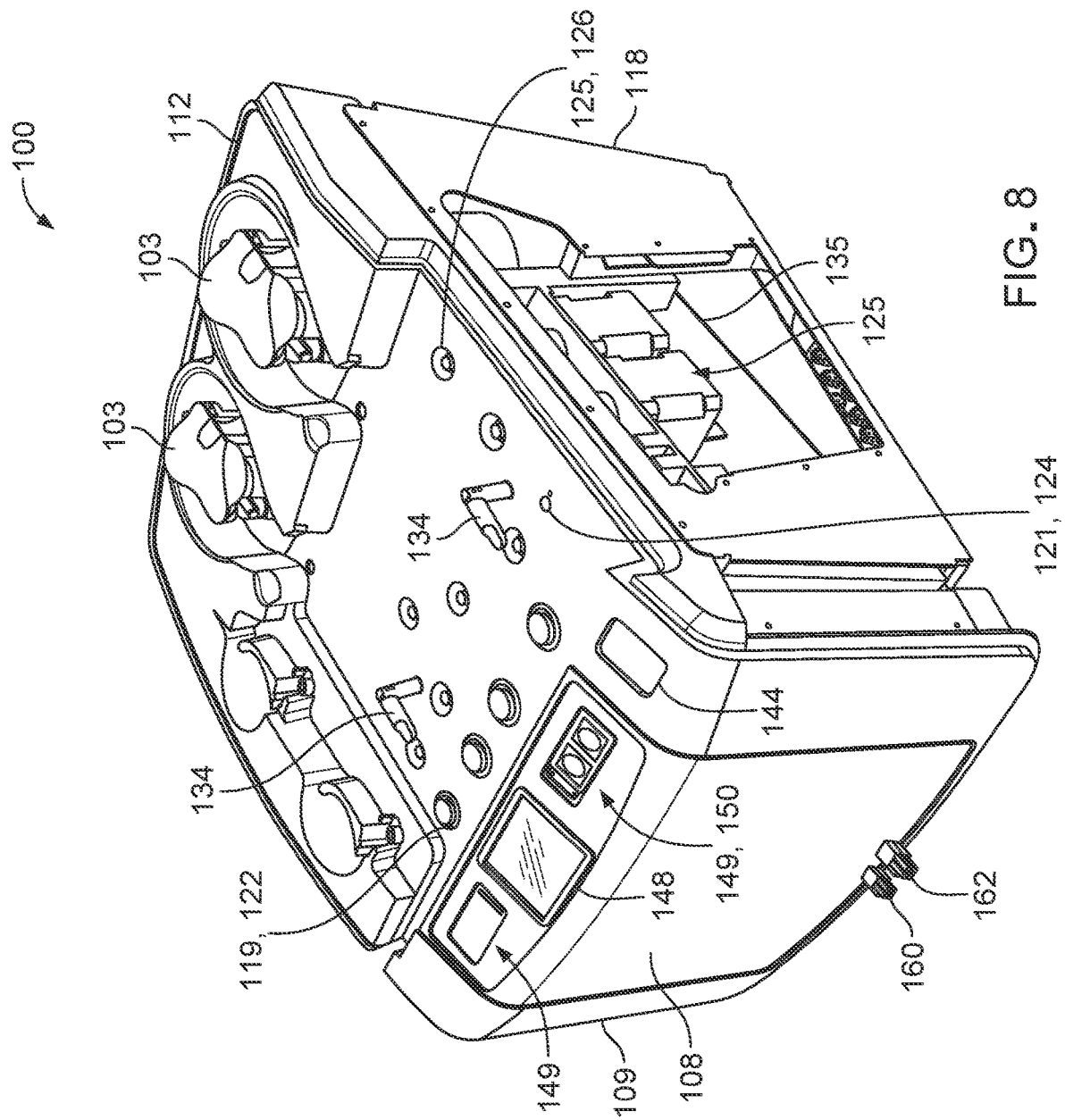
FIG. 8 is a perspective view of the fluid conditioning system of FIG. 1, with certain exterior components omitted to expose certain interior components.

FIGS. 6-8 illustrate certain interior components of the fluid conditioning system 100. For example, the fluid conditioning system 100 further includes multiple pressure transducers 119, two temperature sensors 120, and an ammonia sensor 121 that are respectively positioned within holes 122, 123, 124 in the upper panel 112 for engagement with the fluid cassette 102. The pressure transducers 119 are embodied as thin, flexible membranes that contact corresponding thin, flexible membranes 164 within the fluid cassette 102 (refer to FIG. 15) for detecting fluid pressures within certain fluid pathways of the fluid cassette 102. The temperature sensors 120 are infrared (IR) sensors that detect temperatures of the dialysate flowing through certain points of the fluid pathways of the fluid cassette 102. The ammonia sensor 121 is a red-green-blue (RGB) color sensor that can detect color changes on a paper strip within the fluid cassette 102 to measure a concentration of ammonium within the dialysate flowing through a certain fluid pathway of the fluid cassette 102. The fluid conditioning system 100 also includes circuitry that acquires and conditions signals generated by conductivity sensors that are provided on the fluid cassette 102, which will be discussed in more detail below.

The fluid conditioning system 100 also includes multiple actuators 125 that are aligned with holes 126 in the upper panel 112 for respectively and selectively moving multiple valves of the fluid cassette 102. Each actuator 125 is mounted to a platform 127 of an internal frame 128 of the fluid conditioning system 100 and includes a motor 129 and a drive unit 130 that can be moved (e.g., rotated or otherwise manipulated) by the motor 129. The drive unit 130 is equipped with a coupling member 131 that is formed to engage a respective valve of the fluid cassette 102 such that movement of the drive unit 130 produces movement of the valve. The internal frame 128 also includes columnar support members 132 that support and locate the upper panel 112 of the housing 101. The upper panel 112 further defines holes 133 that are positioned and sized to receive locating pins 134 for appropriately positioning the fluid cassette 102 with respect to the upper panel 112. With the fluid cassette 102 in place, the locating pins 134 can be snapped down toward the upper panel 112 to lock the position of the fluid cassette 102. The fluid conditioning system 100 also includes a circuit board 135 equipped with electronics for operating the various electromechanical components of the fluid conditioning system 100. For example, the electronics execute codes for carrying out the various stages of a fluid conditioning cycle (as discussed below with reference to FIGS. 18-20), operating the pumps 103, 104, turning valves for the fluid cassette 102, processing sensor signals, operating the actuators 125, operating a heater assembly 151, and running control loops (e.g., control loops for regulating dialysate temperature, regulating pump speeds to achieve desired flow rates, regulating pump speeds to achieve desired dialysate chemical compositions, and ensuring device safety).

Referring again to FIG. 5, the fluid conditioning system 100 further includes a support bracket 136 and a fan 137 carried therein for cooling the circuit board 135 and other internal components of the fluid conditioning system 100. The fluid conditioning system 100 also includes a power supply 138, as well as a support bracket that carries an A/C-in port 140.

Figure 10:
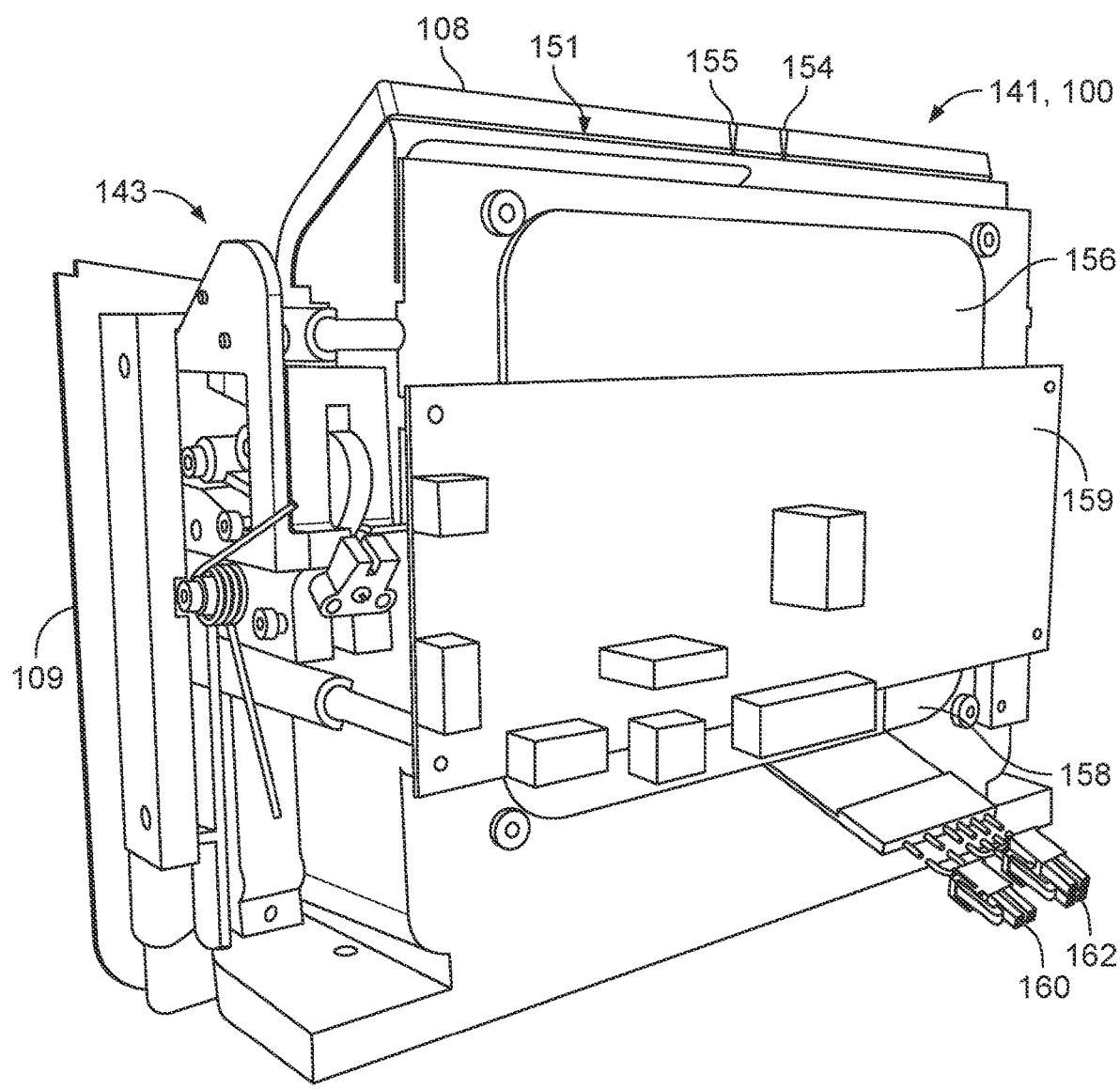
FIG. 10 is a rear perspective view of the front assembly of FIG. 9.
Figure 11:
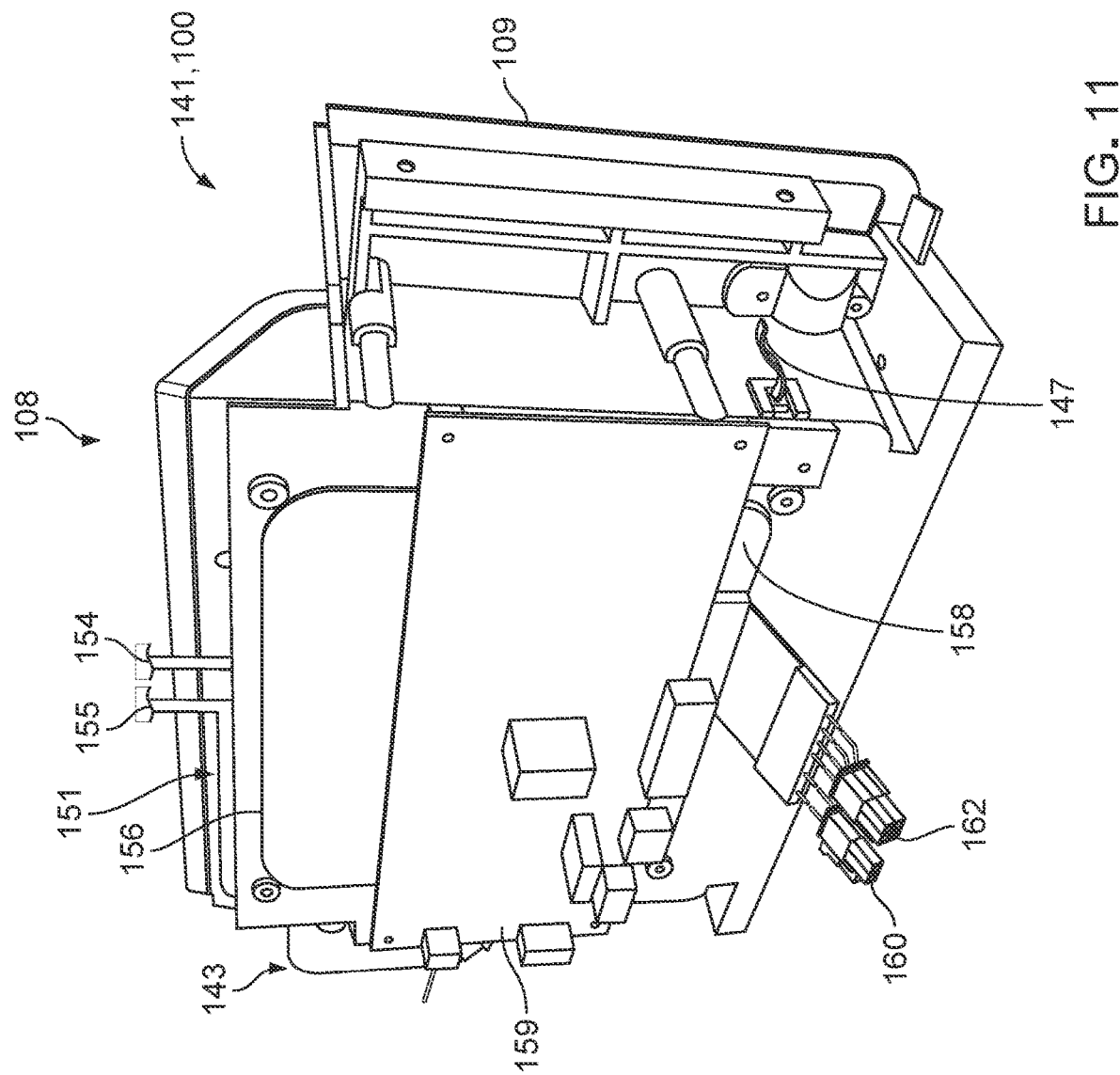
FIG. 11 is a rear perspective view of the front assembly of FIG. 9.
Figure 12:
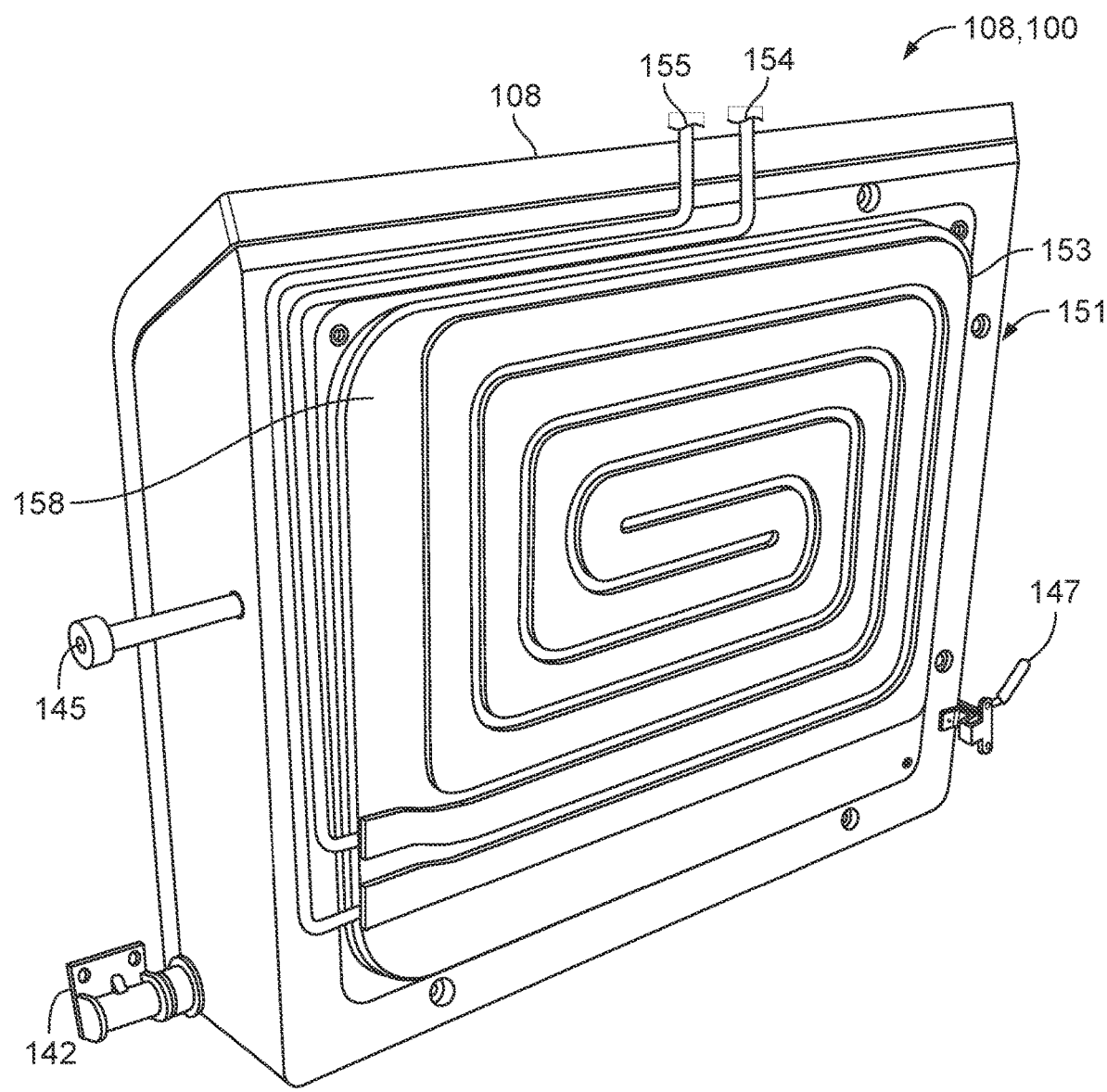
FIG. 12 is a rear perspective view of a heater bag of a door assembly of the front assembly of FIG. 9.

FIGS. 9-13 illustrate various views of a front assembly 141 of the fluid conditioning system 100. The front assembly 141 includes the door assembly 108 and the front panel 109 of the housing 101. The door assembly 108 is pivotable at hinges 142 with respect to the front panel 109 to allow loading of the heater bag 153 into the fluid conditioning system 100. The hinges 142 are friction hinges located along opposite sides of the door assembly 108, as shown in FIG. 12.

Figure 13:
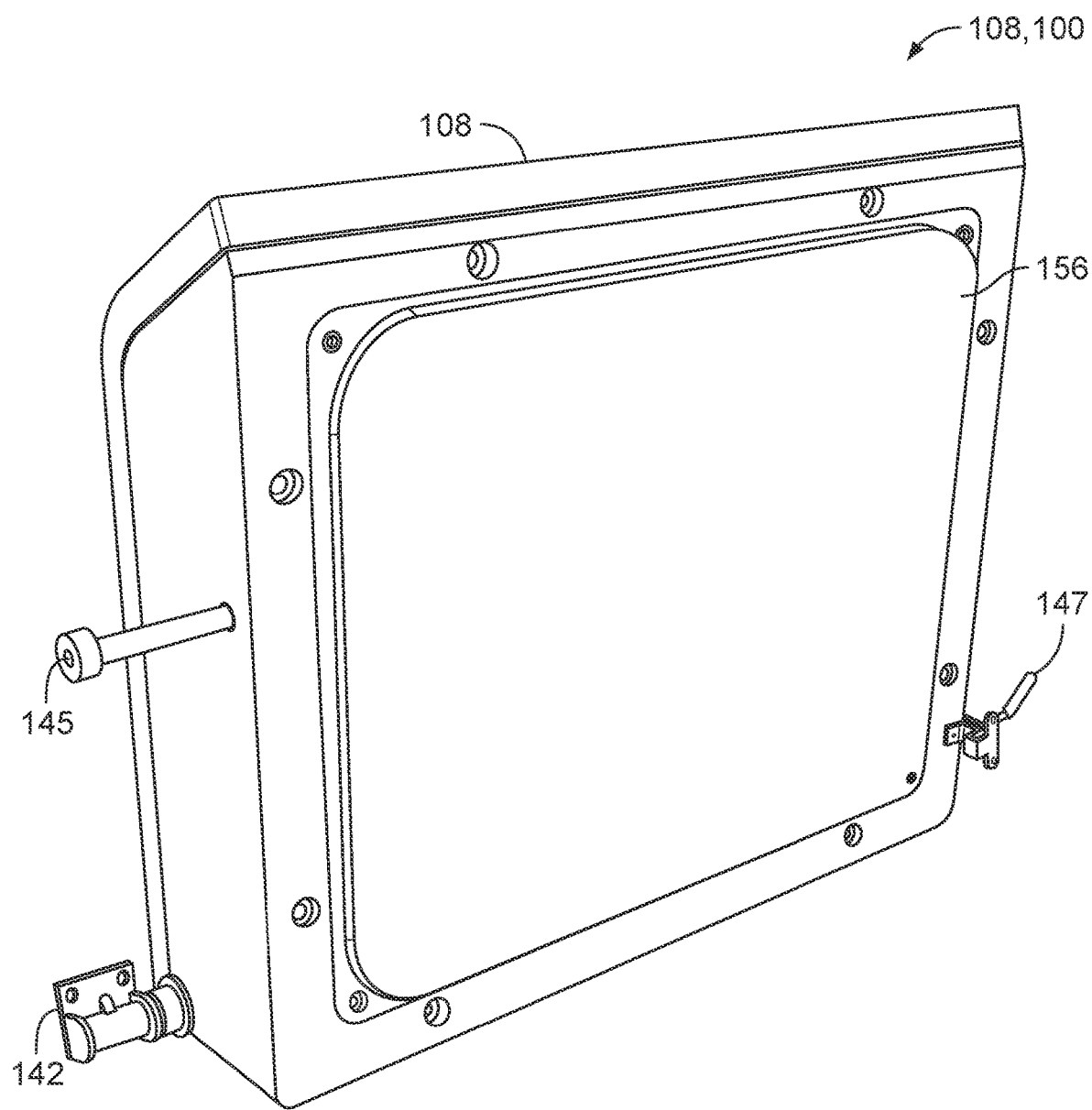
FIG. 13 is a rear perspective view of a heater plate of a door assembly of the front assembly of FIG. 9.

The front panel 109 carries a latch assembly 143 that cooperates with a button 144 carried by the upper panel 112 (shown in FIGS. 1-4) to releasably secure the door assembly 108 to the front panel 109 in a closed position. For example, depression of the button 144 adjusts the latch assembly 143 so that the door assembly 108 can be unlocked from a closed position and pivoted to an open position. The door assembly 108 can alternatively be pivoted inward from an open configuration until oppositely positioned screws 145 (e.g., shoulder screws, shown in FIG. 12) engage the latch assembly 131 to lock the door assembly 108 in the closed position. The latch assembly 131 has a contact switch for determining whether the door assembly 108 is open or closed. Referring particularly to FIGS. 11 and 13, the door assembly 108 includes an optical switch 147 that indicates whether or not the heater bag is inserted. In some embodiments, the fluid conditioning system 100 may be inoperable when the door assembly 108 is open.

Figure 9:
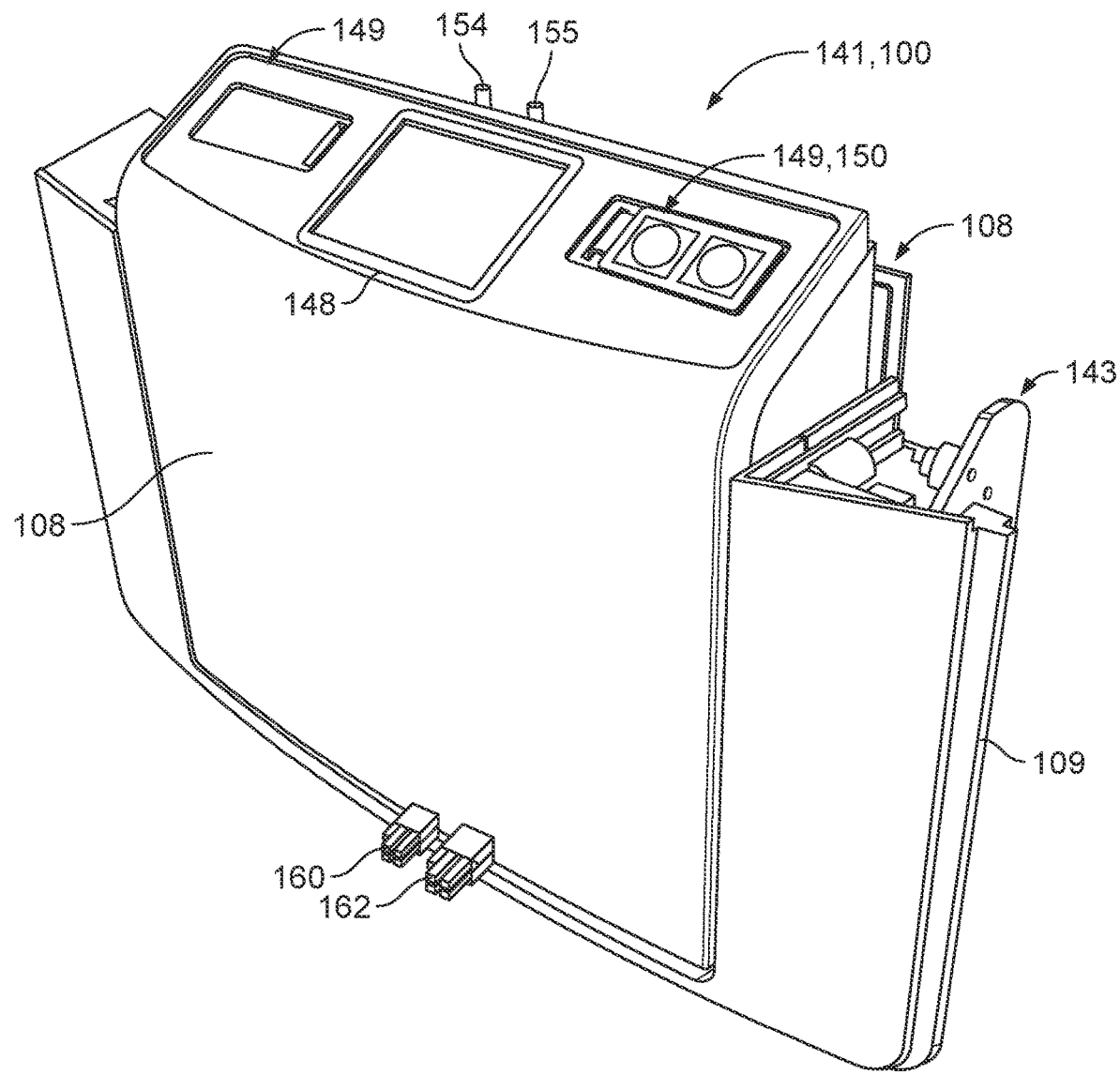
FIG. 9 is a perspective view of a front assembly of the fluid conditioning system of FIG. 1.

Referring particularly to FIG. 9, the door assembly 108 supports a display screen 148 (e.g., a touchscreen display) on which graphical user interfaces (GUIs) can be displayed and two control panels 149 that can each be equipped with selectors 150 (e.g., buttons) for providing inputs at the GUIs to operate the fluid conditioning system 100. Example parameters and processes that may be controlled by a user via the display screen 148 using the selectors 150 include starting and stopping a treatment, initiating a drain cycle, changing a flowrate, a priming stage of a fluid conditioning cycle, initiating system preparation to start a fluid conditioning cycle, adjusting a temperature according to patient comfort, and confirming correct placement of the fluid cassette 102, or fluid lines that interface with the pumps 103, 104.

Referring to FIGS. 10-13, the front assembly 141 includes components of a heater assembly 151 that is designed to regulate fluid temperatures of dialysate transported along the fluid pathways of the fluid cassette 102. Referring particularly to FIG. 12, the heater assembly 151 includes a heater bag 153 that is equipped with an input connection 154 and an output connection 155 that can interface with the fluid cassette 102 for allowing dialysate to circulate through the heater bag 153 to be warmed. The heater bag 153 is formed as a plastic channel that has a generally flat, collapsed shape when empty, that inflates upon filling with fluid, and that transfers heat from an exterior surface to dialysate flowing through the heater bag 153.

Figure 14:
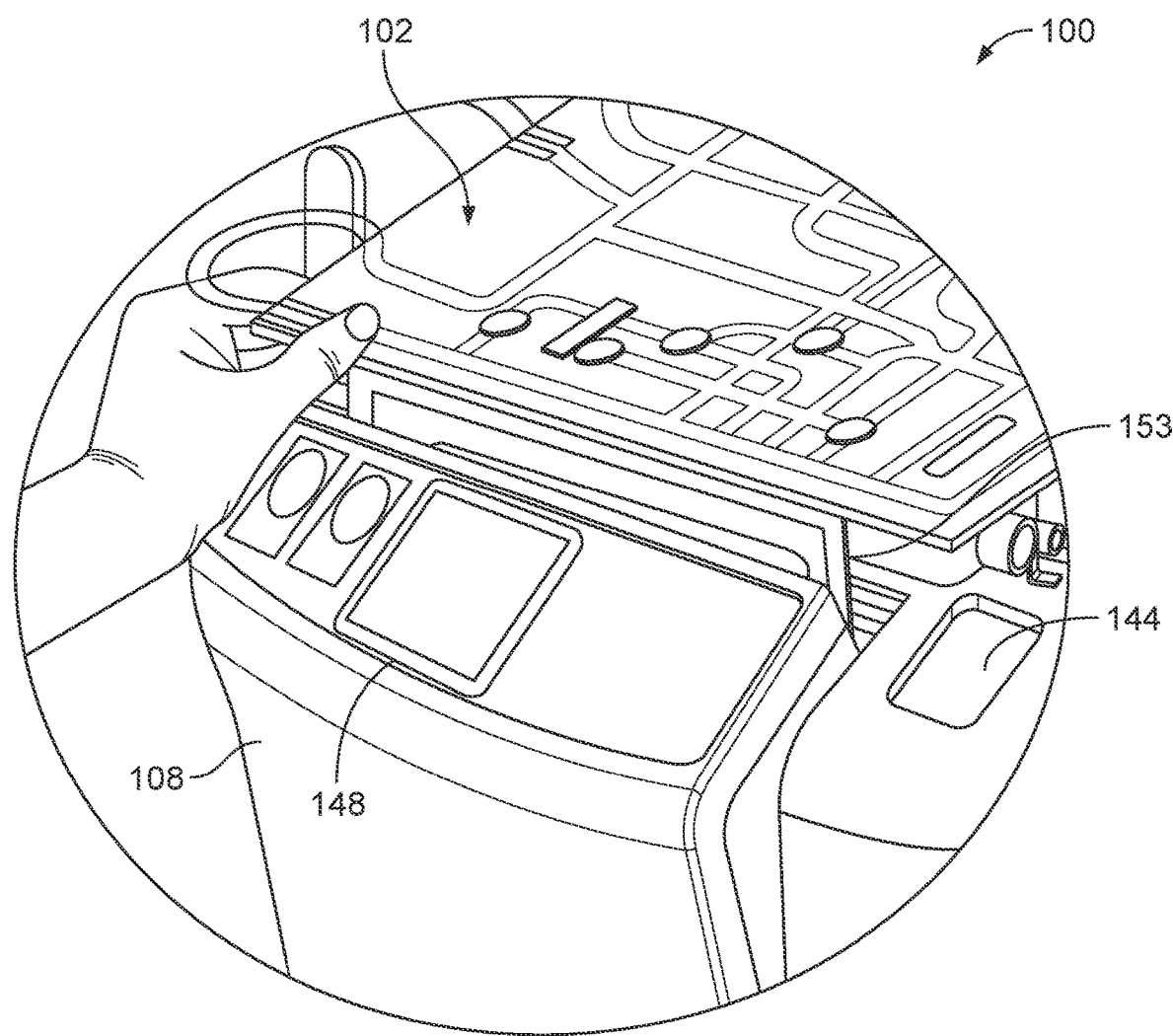
FIG. 14 is a perspective view illustrating installation of the heater bag of FIG. 12 and a fluid cassette of the fluid conditioning system of FIG. 1.

Referring as well to FIGS. 13 and 14, the heater assembly 151 further includes two plates 156 that position and support the heater bag 153 and that are heated for transferring heat to fluid within the heater bag 153. For example, with the door assembly 108 in the open configuration, the heater bag 153 can be slid between heater plates 156. Referring particularly to FIGS. 10-12, the heater assembly 151 further includes a heating element by which fluid in the heater bag 153 can be warmed and two insulation pads 158 disposed on opposite sides of the heater bag 153, or an arrangement with {insulation pad} {heating pad} {metal plate} {heater bag} {metal plate} {heating pad} {insulation pad}. The heating element is attached to a metal (e.g., aluminum) plate 156. The heater assembly 151 also includes a circuit board 159 that provides electronics for operating the heater assembly 151, a feed line 160 for each heating pad 156 that provides power, and thermocouple connections 162 for determining a temperature of the respective heating plates 156.

Figure 15:
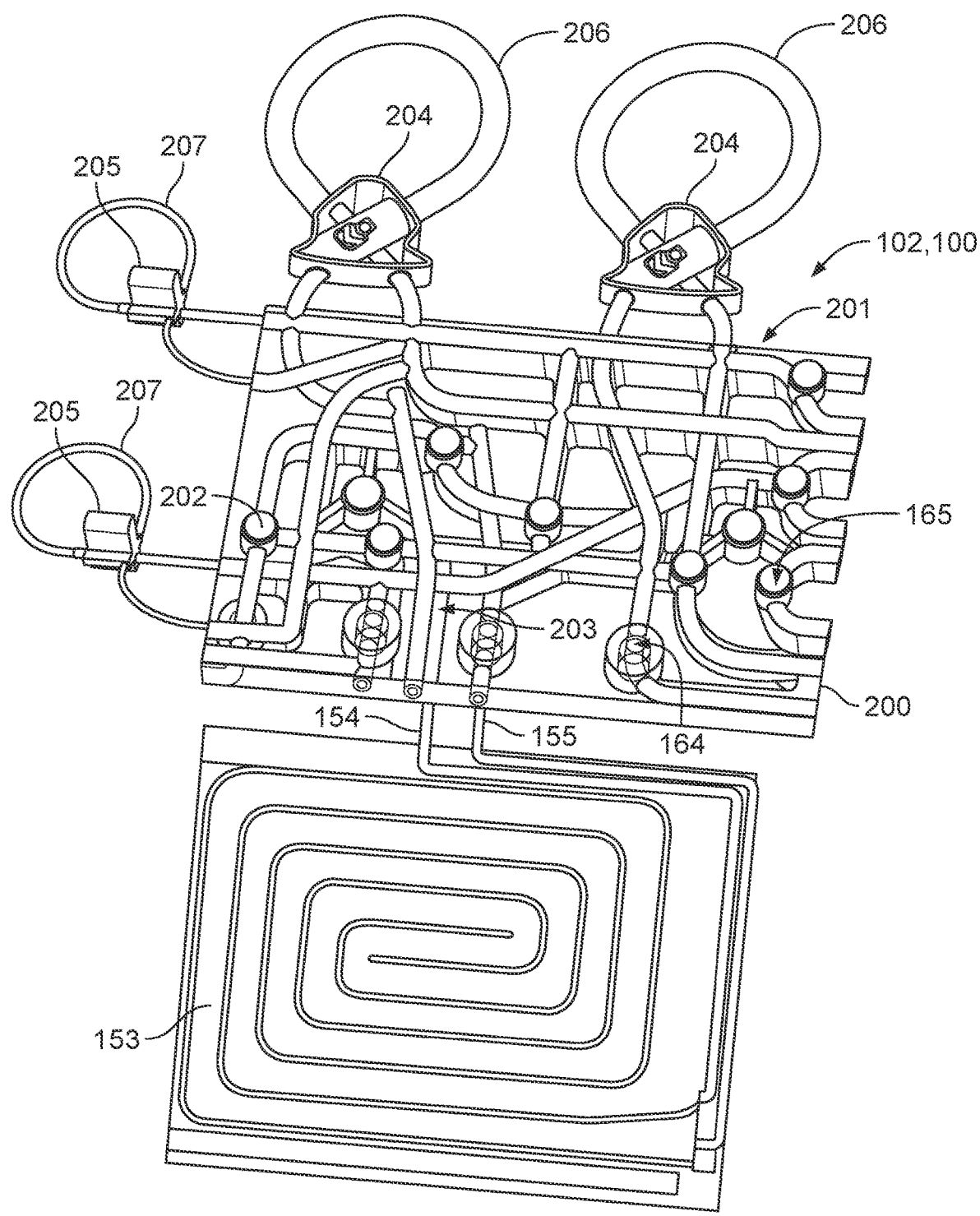
FIG. 15 is a perspective view of the fluid cassette of FIG. 14, along with the heater bag of FIG. 12.

Referring to FIG. 15, the fluid cassette 102 is a single-use, disposable cartridge that includes a housing 200, multiple fluid lines 201 arranged within the housing 200, multiple valves 202 positioned along the fluid lines 201, two conductivity sensors 203 positioned along the fluid lines 201, two fluid line connectors (e.g., pump segment clips) 204, and two fluid line connectors (e.g., pump segment clips) 205. The fluid lines 201 cooperate with the heater bag 153 and a dialysis system to form a fluid circuit 350 for carrying out a fluid conditioning cycle. For example, the fluid lines 201 include ports to which the input and output connections 154, 155 of the heater bag 153 can be connected for providing fluid communication between the fluid lines 201 and the heater bag 153. The fluid line connectors 204 locate fluid line segments 206 about the high-capacity pumps 103, and the fluid line connectors 205 locate fluid line segments 207 about the low-capacity pumps 104. The fluid cassette 102 also includes additional fluid lines that extend from the fluid cassette 102 to various fluid containers, as illustrated in FIG. 17.

The valves 202 are three-way valves by which two alternative fluid pathways can be selected by a control system of the fluid conditioning system 100. Lower portions of the valves 202 are formed to engage with the coupling members 131 of the actuators 125 for movement of the valves 202. Example types of valves 202 that may be included in the fluid cassette 102 include rotary valves, push-pull valves, sliding valves, and shuttle valves.

Figure 16:
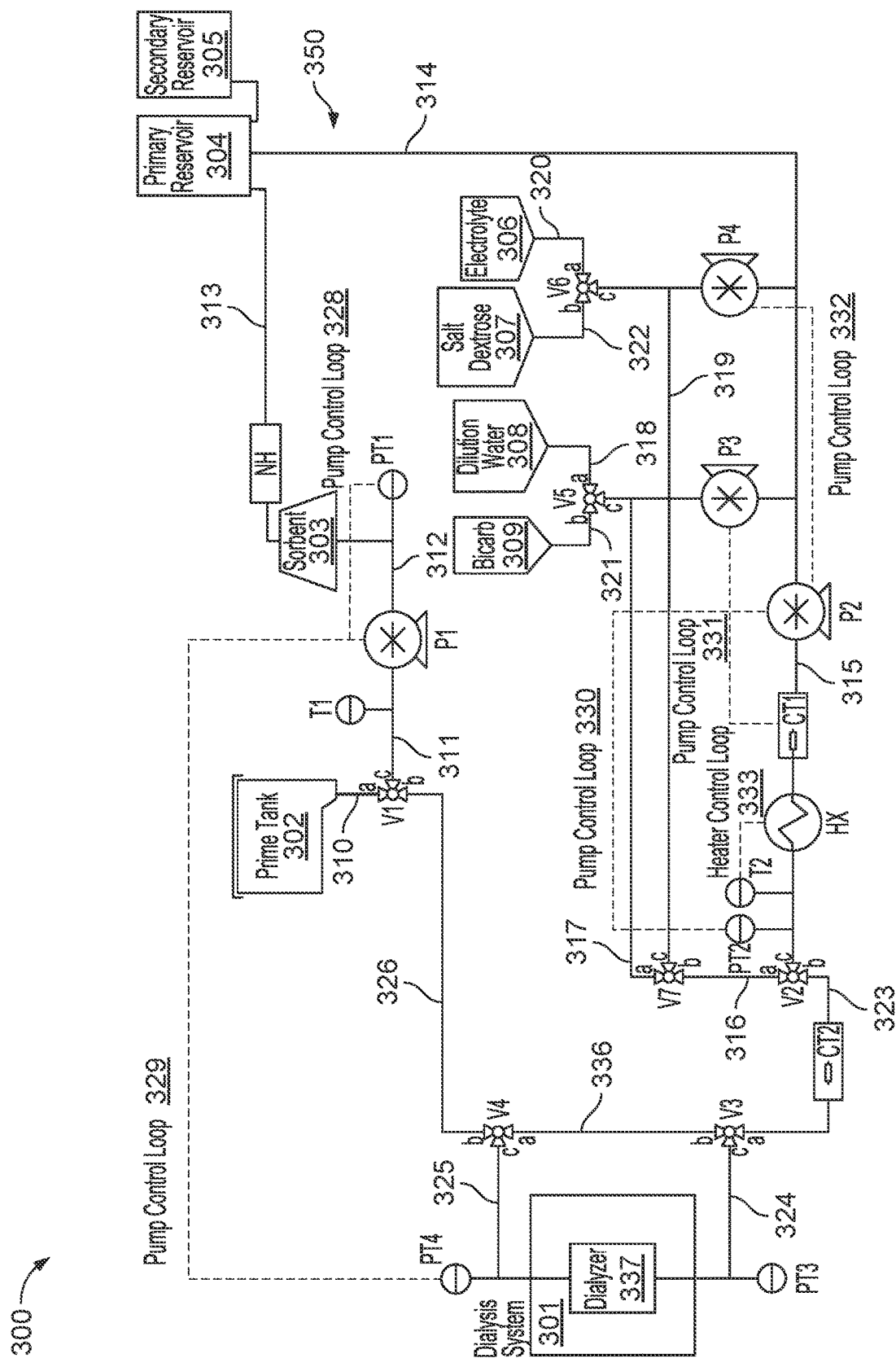
FIG. 16 provides an operational diagram by which the fluid conditioning system of FIG. 1 can cooperate with a dialysis system to form a fluid circuit for carrying out the fluid conditioning cycle.
Figure 17:
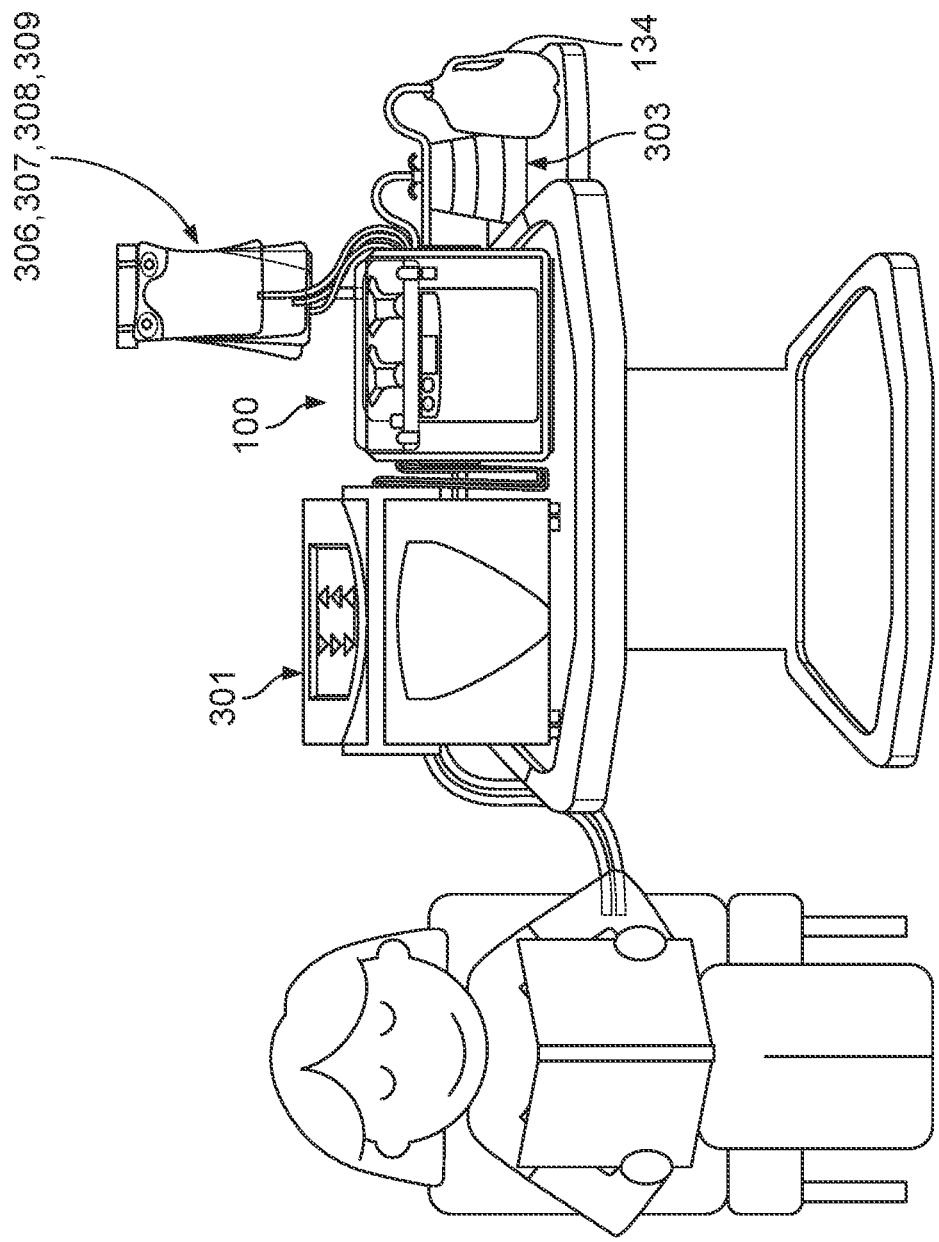
FIG. 17 illustrates an example setup of the fluid conditioning system of FIG. 1 with the dialysis system of FIG. 16.

FIG. 16 illustrates an operational diagram 300 by which the fluid conditioning system 100 can cooperate with a dialyzer 337 of a dialysis system 301 to form the fluid circuit 350 (indicated by solids lines) for carrying out a fluid conditioning cycle, while FIG. 17 illustrates an example setup of the fluid conditioning system 100 with the dialysis system 301. Example types of dialysis systems 301 that may be coupled to the fluid conditioning system 100 include HD systems, PD systems, HF systems, and HDF systems. The fluid circuit 350 incorporates components of the fluid cassette 102, as well as various other components of the fluid conditioning system 100.

For example, in addition to the components discussed above with respect to FIGS. 1-15, the fluid conditioning system 100 also includes a control system 161 (e.g., including the circuit boards 135, 159, as well as additional circuit boards for sensor circuitry) for controlling various operations of the fluid conditioning system 100 and several other, peripheral components positioned along the fluid circuit 350. These components include a prime tank 302 for collecting water to produce dialysate (e.g., sometimes referred to as dialysis fluid), a sorbent cartridge 303 for filtering tap water to provide purified water suitable for creating dialysate and for cleansing dialysate exiting the dialysis system 301, a primary reservoir 304 for collecting fluid (e.g., unconditioned water or dialysate) exiting the sorbent cartridge 303, a secondary reservoir 305 for collecting fluid that exceeds a capacity of the primary reservoir 304, a bag 306 for containing an electrolyte solution, a bag 307 for containing a salt-dextrose (SD) solution, a bag 308 for containing dilution water (DW), and a bag 309 for containing a bicarbonate (BC) solution that are positioned along the fluid flow path arrangement 300.

The bags 306, 307, 309 are pre-loaded with appropriate amounts of dry chemicals that can be dissolved in water to produce the electrolyte solution, the salt-dextrose solution, and the bicarbonate solution. Each bag 306, 307, 309 includes a nozzle that is designed to increase a velocity of a fluid flow entering the bag 306, 307, 309 and to create turbulence needed for adequate mixing and dissolution of the dry chemicals in water.

Table 1 lists approximate capacities of the various fluid-containing components of the fluid conditioning system 100.

TABLE 1

Capacities of fluid-containing components of the fluid conditioning system 100.

| Component | Capacity (mL) |
| --- | --- |
| Prime Tank (302) | 8000 |
| Primary Reservoir (304) | 7500 |
| Secondary Reservoir (305) | 4500 |
| Electrolyte Bag (306) | 500 |
| Salt/Dextrose Bag (307) | 160 |
| Dilution Water Bag (308) | 4000 |
| Bicarbonate Bag (309) | 1000 |

The three-way valves 202 of the fluid cassette 102 are indicated as V1-V7 in the fluid circuit 350. Each valve includes three fluid ports (a), (b), (c) by which a flow path in the valve can be adjusted. A valve may be referred to as closed when two or three of its ports are closed and may be referred to as open when two or three of its ports are open. The valves include a prime valve V1, a dissolution valve V2, a bypass out valve V3, a bypass in valve V4, a BC/DW valve V5, an S/D/Electrolyte valve V6, and a condo salt selector valve V7. The fluid lines 201 of the fluid cassette 102 will be referenced individually further below with respect to an operation of the fluid conditioning system 100. The high-capacity pumps 103 and the low-capacity pump 104 of the fluid conditioning system 100 are indicated respectively as P1, P2 and P3, P4 in the fluid circuit 350. The pumps include a cassette-in pump P1, a dialysate pump P2, a conductivity control pump P3, and an electrolyte/salt-dextrose pump P4. Table 2 lists approximate operational (e.g., fluid flow rate) ranges of the pumps P1-P4.

TABLE 2

Operational ranges of pumps of the fluid conditioning system 100.

| Pump | Operational Range (mL/min) |
| --- | --- |
| P1 | 20-600 |
| P2 | 20-600 |
| P3 | 0.1-100 |
| P4 | 0.1-100 |

The heater assembly 151 and the ammonia sensor 121 of the fluid conditioning system 100 are respectively indicated as a heat exchanger HX and an ammonia sensor NH in the fluid circuit 350. The conductivity sensors 203 of the fluid cassette 102 are indicated as a conductivity sensor CT1 associated with a fluid temperature upstream of the heat exchanger HX and a conductivity sensor CT2 associated with a fluid temperature downstream of the heat exchanger HX. In addition to having a capability measure fluid conductivity, conductivity sensors CT1 and CT2 also have a capability to measure fluid temperature. Given that conductivity changes with temperature, the temperatures measured by the conductivity sensors CT1 and CT2 may, in some implementations, be used to correct conductivity values measured by the conductivity sensors CT1 and CT2 to provide temperature-compensated conductivity measurements. In some implementations, a fluid temperature measured by the conductivity sensor CT2 may also provide a safety check on a final temperature of dialysate that exits the fluid conditioning system 100 to flow into the dialysis system 303. The temperature sensors 120 of the fluid conditioning system 100 are indicated as a cassette-in temperature sensor T1 and a heat exchanger temperature sensor T2 in the fluid circuit 350. The pressure transducers 119 of the fluid conditioning system 100 are indicated as pressure transducers PT1, PT2, PT3, and PT4 in the fluid circuit 350.

The fluid conditioning system 100 can be operated in multiple stages to cooperate with the dialysis system 301 (e.g., with the dialyzer 337) for carrying out a fluid conditioning cycle in which a dialysis treatment is administered to a patient via the dialysis system 301. For example, the fluid conditioning cycle includes a priming stage, an infusion stage, and a treatment stage. The fluid conditioning cycle typically has a total duration of about 135 min to about 300 min.

Figure 18:
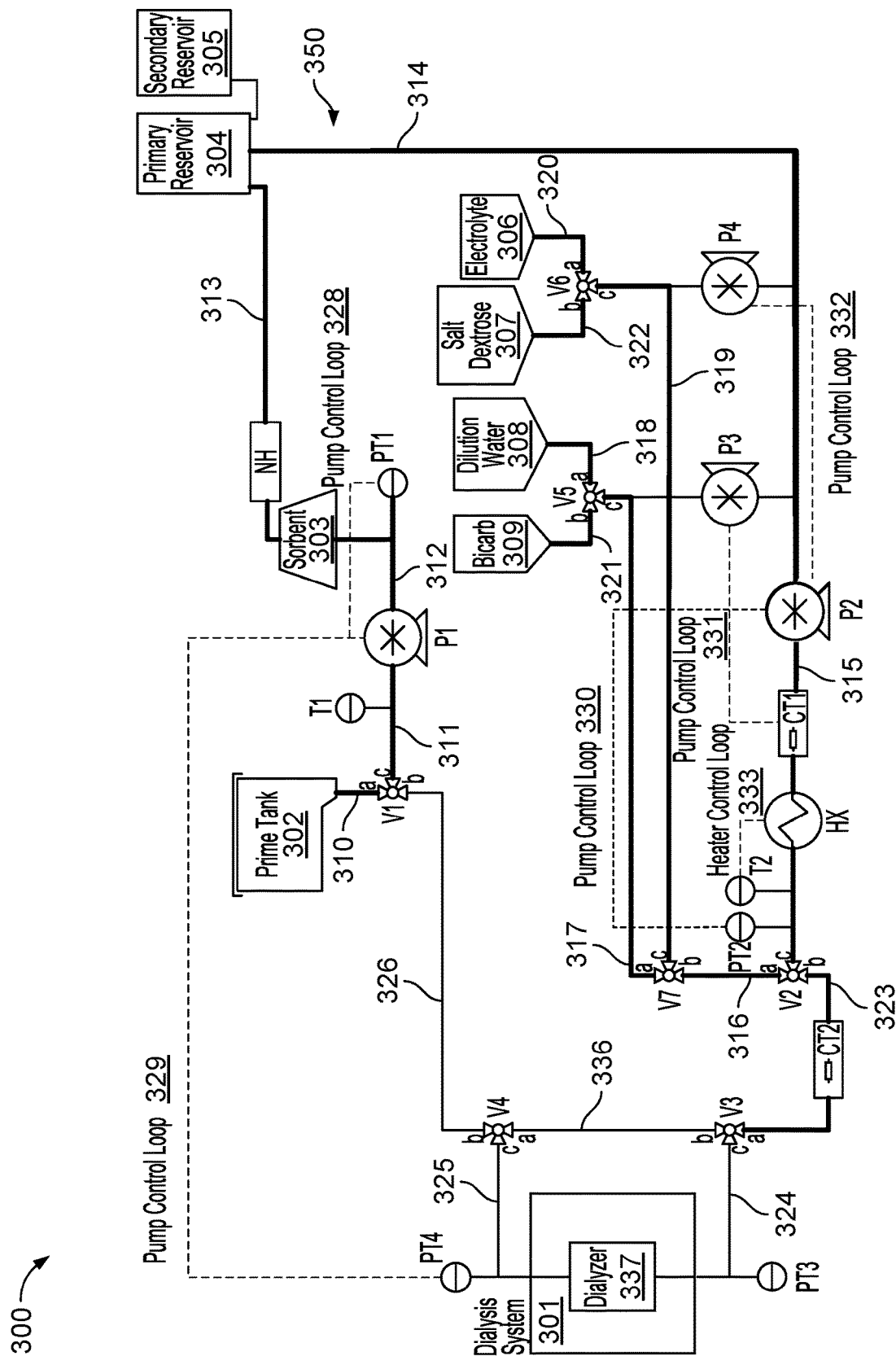
FIG. 18 illustrates a fluid flow path (indicated by highlighted bolded fluid lines) of a priming stage of the fluid conditioning cycle carried out via the fluid circuit of FIG. 16.

FIG. 18 illustrates operation of the fluid conditioning system 100 during the priming stage, in which an initial volume of water is drawn into the fluid circuit 350 for subsequent creation of dialysate. At the beginning of the priming stage, the prime tank 302 is filled to about 7.6 L with water (e.g., tap water, bottled water, reverse osmosis water, distilled water, or drinking water) from a water source (e.g., a container 134 of water, shown in FIG. 17), pump P1 is turned on, and heat exchanger HX is turned on. The water is pumped by pump P1 from the prime tank 302 into a fluid line 310, through ports (a) and (c) of valve V1, into a fluid line 311, past temperature sensor T1, and into pump P1. At this stage of operation, pump P1 pumps water at a flow rate in a range of about 200 mL/min to about 600 mL/min, and heat exchanger HX is powered to maintain a fluid temperature at a set point in a range of about 15° C. to about 42° C.

If temperature sensor T1 detects a water temperature of greater than about 42° C., then a message is displayed on the display screen 148 to advise a user that the water temperature is too warm, valve V1 is closed, and pump P1 is turned off and to prevent additional water from entering the fluid circuit 350. If temperature sensor T1 detects a water temperature of less than or equal to about 42° C., then ports (a) and (c) of valve V1 remain open, and pump P1 pumps the water through a fluid line 312 into the sorbent cartridge 303, into a fluid line 313, past ammonia sensor NH, and into the primary reservoir 304. At this stage of operation, the sorbent cartridge 303 purifies the water circulating in the fluid circuit 350, such that the water meets or exceeds water quality standards for drinking water as set by the Environmental Protection Agency (EPA) and water quality standards for hemodialysis water as set by the Association for the Advancement of Medical Instrumentation (AAMI) standard.

Once the primary reservoir 304 collects about 100 mL to about 500 mL of water, then pump P2 is turned on and pumps water into a fluid line 314, through pump P2, into a fluid line 315, past conductivity sensor CT1, and past the heat exchanger HX1, which heats the water in the fluid line 315 to the set point temperature. Pump P2 is controlled to pump water at a flow rate that is about equal to the flow rate at which water is pumped by pump P1. Water moves from the fluid line 315 through ports (c) and (a) of valve V2, into a fluid line 316, through ports (b) and (a) of valve V7, into a fluid line 317, through ports (c) and (a) of valve V5, into a fluid line 318, and further into the bag 308 until the bag 308 is filled to about 3.5 L to about 4.0 L with water (e.g., dilution water).

Next, ports (a) and (c) of valve V5 are closed, port (a) of valve V7 is closed, and port (c) of valve V7 is opened such that the pump P2 pumps water into a fluid line 319, through ports (c) and (a) of valve V6, into a fluid line 320, and further into the bag 306 until the bag 306 is filled to capacity with water to produce the electrolyte solution. Ports (a) and (c) of valve V6 are closed, port (a) of valve V7 is closed, port (c) of valve V7 is reopened, and ports (b) and (c) of valve V5 are opened. Pump P2 then pumps water into the fluid line 317, through ports (c) and (b) of valve V5, into a fluid line 321, and further into the bag 309 until the bag 309 is filled to capacity with water to produce the bicarbonate solution.

At this point in the priming stage, the set point temperature of the heat exchanger HX is increased to a range of about 31° C. to about 39° C. (e.g., where 39° C. is the maximum temperature achievable by heat exchanger HX), and the flow rate of pump P2 is reduced to a value within a range of about 100 mL/min to about 300 mL/min to increase an exposure time of the water within the heat exchanger HX for achieving the higher set point temperature. Ports (b) and (c) of valve V5 are closed, port (a) of valve V7 is closed, port (c) of valve V7 is opened, and ports (b) and (c) of valve V6 are opened. Accordingly, pump P2 pumps water into the fluid line 319, though ports (c) and (b) of valve V6, into a fluid line 322, and further into the bag 307 until the bag 307 is filled to capacity to produce the salt-dextrose solution. The higher set point temperature of heat exchanger HX facilitates dissolution of the salt-dextrose substance with the water flowing into the bag 309. At this point during the fluid conditioning cycle, the priming stage concludes, the prime tank 302 has substantially emptied, the pumps P1, P2 are turned off and the infusion stage can begin. The priming stage typically lasts a duration of about 10 min to about 30 (e.g., about 20 min).

Figure 19:
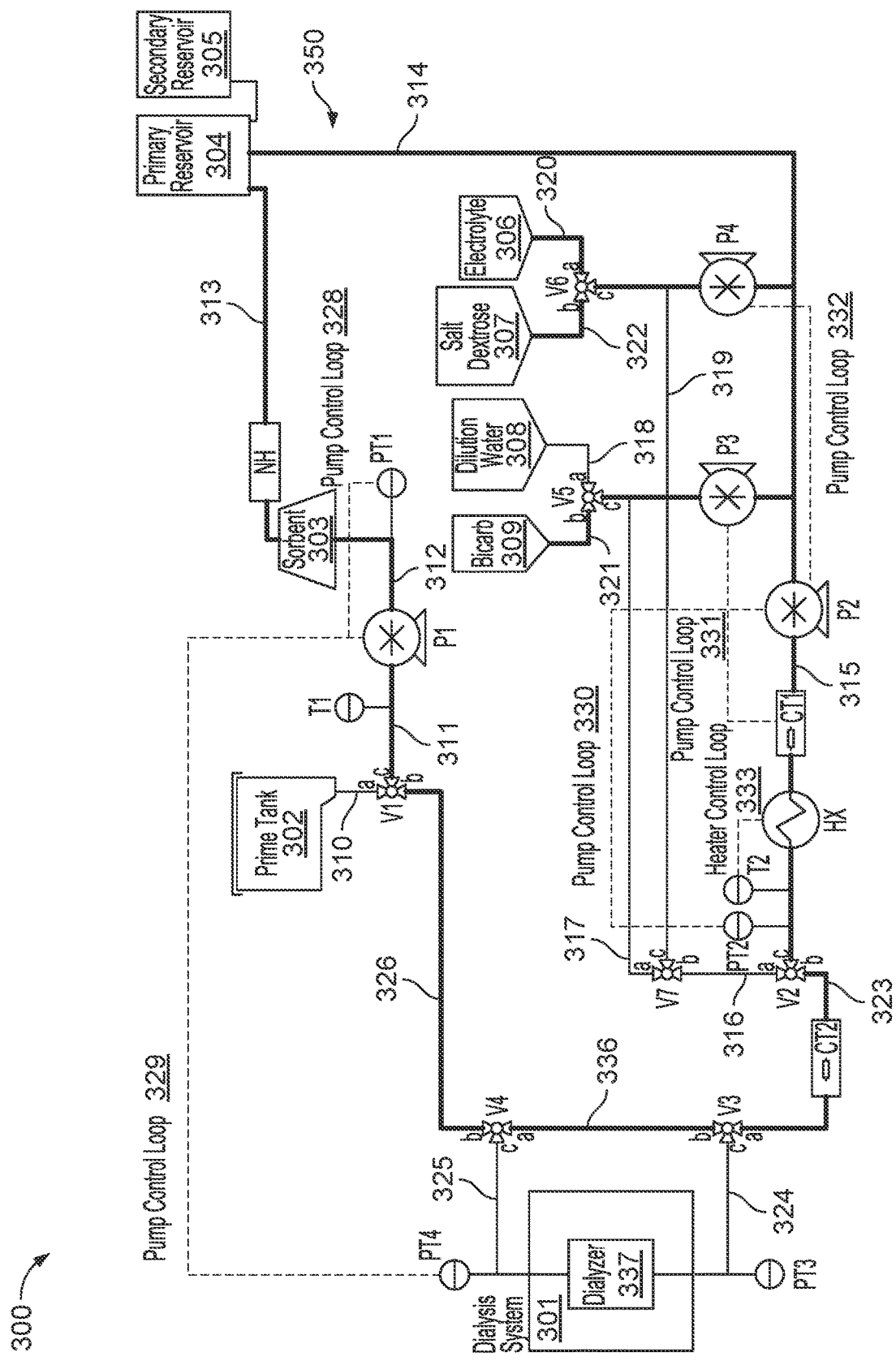
FIG. 19 illustrates a fluid flow path (indicated by highlighted bolded fluid lines) of an infusion stage of the fluid conditioning cycle carried out via the fluid circuit of FIG. 16.

FIG. 19 illustrates operation of the fluid conditioning system 100 during the infusion stage, in which bicarbonate, salt, and dextrose are added to the water in the fluid circuit 350 to produce dialysate. In particular, bicarbonate, salt, and dextrose are added to the water in a controlled manner (e.g., under flow rate control) until the salt and dextrose reach physiologically acceptable concentrations and until the bicarbonate yields a physiologically acceptable fluid conductivity and fluid pH. During the infusion stage, heat exchanger HX is powered to maintain a fluid temperature at a set point in a range of about 35° C. to about 39° C.

At the beginning of the infusion stage, valve V7 is closed, port (a) of valve V2 closes, port (b) of valve V2 opens, ports (a) and (b) of both valves V3 and V4 open, port (b) of valve V1 opens, port (a) of valve V1 closes, ports (b) and (c) of valve V6 remain open, and ports (b) and (c) of valve V5 open. Pumps P1, P2 are immediately turned on to pump water at a flow rate in a range of about 300 mL/min to about 600 mL/min within the fluid circuit 350. At the same time, pumps P3 and P4 are turned on. Pump P3 pumps bicarbonate solution out of the bag 309 at a flow rate of about 10 mL/min to about 100 mL/min, into the fluid line 317, through the pump P3, and into the fluid line 314. Pump P4 pumps salt-dextrose solution out of the bag 307 at a variable flow rate into the fluid line 319, through pump P4, and into the fluid line 314. The flow rate at which P4 initially pumps fluid is in a range of about 1 mL/min to about 100 mL/min. The flow rate is gradually stepped down by a factor of 2 at periodic time increments of about 1 min. The flow rates of pumps P3 and P4 are set to completely add the infusion volume respectively of the BC solution and the SD solution over a single revolution around the fluid circuit 350. Accordingly, the flow rates of pumps P3 and P4 depend on the flow rates of pumps P1 and P2 during the infusion stage. For example, if the flow rates of pumps P1 and P2 are set to 200 mL/min, then the flow rates of pumps P3 and P4 will be relatively slow. Conversely, if the flow rates of pumps P1 and P2 are set to 600 mL/min, then the flow rates of pumps P3 and P4 will be relatively fast.

Once the bag 307 empties of the salt-dextrose solution, port (b) of valve V6 closes, and port (a) of valve V6 opens to allow pump P4 to pump the electrolyte solution out of the bag 306 at a flow rate of about 0.1 mL/min to about 5 mL/min into the fluid line 314. Once the electrolyte solution reaches valve V3, the infusion stage concludes, and the treatment stage can begin. The dialysate may continue to circulate around the fluid circuit 350 through fluid lines 311, 312, 313, 314, 315, 323, 336, 326 until the treatment stage begins. The infusing stage typically lasts a duration of about 5 min to about 6 min.

Figure 20:
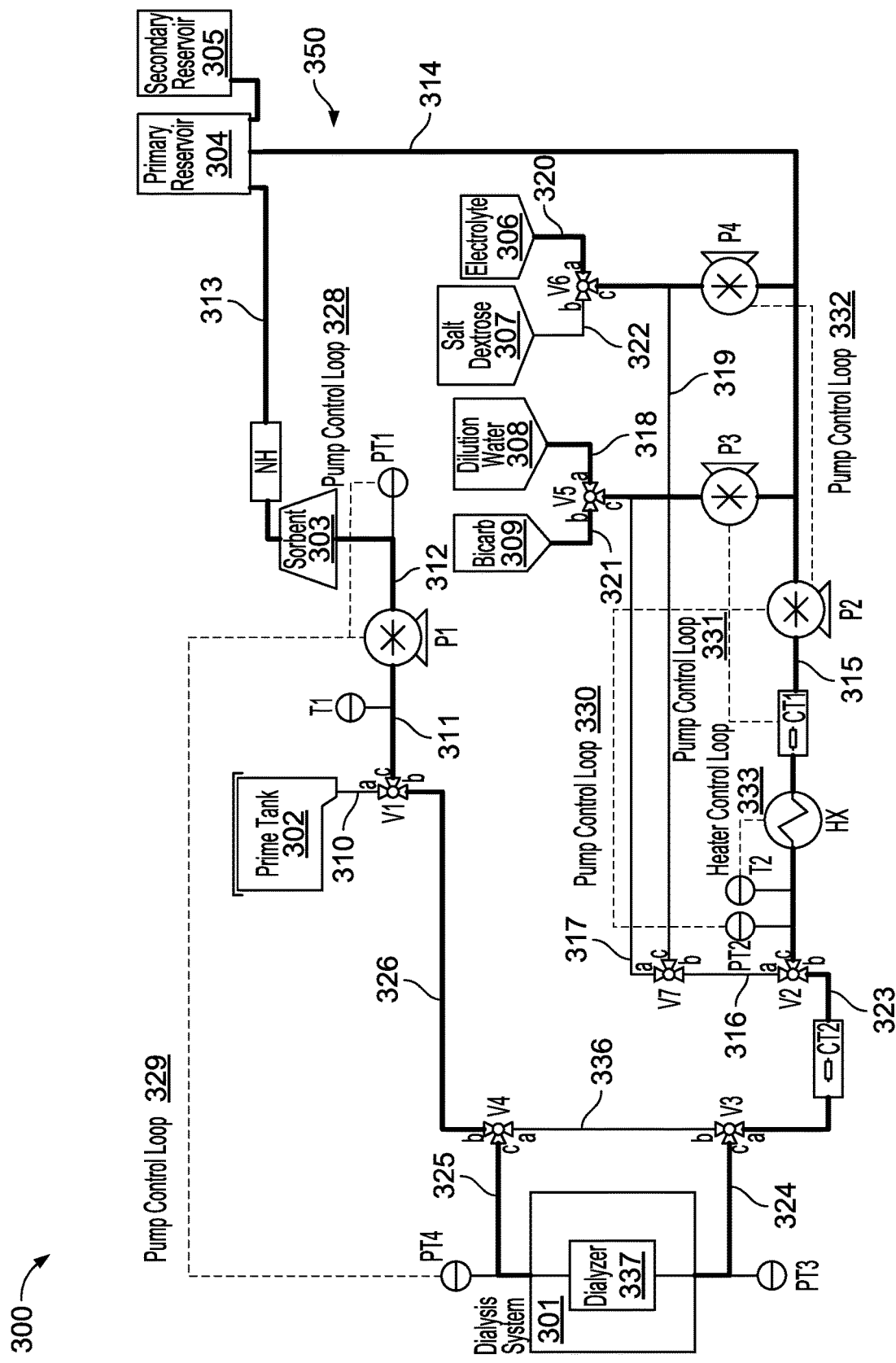
FIG. 20 illustrates a fluid flow path (indicated by highlighted bolded fluid lines) of a treatment stage of the fluid conditioning cycle carried out via the fluid circuit of FIG. 16.

FIG. 20 illustrates operation of the fluid conditioning system 100 during the treatment stage, in which bicarbonate, salt, and dextrose are added to the water in the fluid circuit 350 to produce dialysate. The treatment stage includes a first phase in which bicarbonate solution is used to regulate a conductivity of the dialysate and a second phase in which dilution water is used to regulate a conductivity of the dialysate. Pumps P1, P2 pump dialysate at a flow rate in a range of about 200 mL/min to about 600 mL/min. The set point temperature of heat exchanger HX is maintained at a physiologically acceptable temperature in an acceptable range of about 35° C. to about 39° C. (e.g., about 37° C.), as specifically selected by a user of the fluid conditioning system 100 to suit patient comfort. At any point during the treatment stage, if the dialysate fluid temperature measured at CT2 is outside of a range of about 35° C. to about 42° C., then the fluid conditioning system 100 will enter a bypass mode in which dialysate will flow through fluid line 336 to bypass flow through the dialysis system 301 via fluid lines 324, 325. While the fluid conditioning system 100 is operating in the bypass mode, a message will displayed on the display screen 148 indicating that the fluid temperature is too low or too high. The fluid conditioning system 100 will remain in bypass mode until the fluid temperature stabilizes within the acceptable range.

During the first phase of the treatment stage, port (b) of valve V3 is closed, port (c) of valve V3 is opened to allow pump P2 to pump "fresh" dialysate (e.g., cleaned, conditioned dialysate) through a fluid line 324 and into the dialysis system 301, port (a) of valve V4 is closed, and port (c) of valve V4 is opened to allow pump P1 to pump "spent" dialysate (e.g., contaminated dialysate) through a fluid line 325 out of the dialysis system 301 and further into a fluid line 326. Accordingly, a bypass fluid line 336 that extends between valves V3, V4 is closed. The spent dialysate has been infused with ultra-filtrate from the patient's blood within the dialysis system 301. The ultra-filtrate carries toxic substances, such as urea, all of the small water-soluble uremic toxins, and other toxic substances (e.g., guanidosuccinic acid, methylguanidine, 1-methyladenosine, 1-methylinosine, N2,N2-dimethylguanosine, pseudouridine, arab(in)itol, mannitol, α-N-acetylarginine, orotidine, oxalate, guanidine, erythritol, creatine, orotic acid, phenylacetylglutamine, creatinine, myoinositol, γ-guanidinobutyric acid, β-guanidinopropionic acid, (symmetric dimethyl-arginine) SDMA, asymmetric dimethyl-arginine (ADMA), sorbitol, uridine, and xanthosine).

From the fluid line 326, the spent dialysate is pumped through ports (b) and (c) of valve V1, the fluid line 311, pump P1, the fluid line 312, and into the sorbent cartridge 303. Within the sorbent cartridge 303, the toxic substances are removed from (e.g., filtered out of) the spent dialysate to produce "regenerated" dialysate (e.g., cleaned, unconditioned dialysate) that flows out of the sorbent cartridge 303 and into the fluid line 313, past the ammonia sensor NH, and into the primary reservoir 304. In some cases, a volume of the regenerated dialysate within the primary reservoir 304 exceeds a capacity of the primary reservoir 304 and therefore flows through a fluid line 327 into the secondary reservoir 305, which remains in fluid communication with the primary reservoir 304 throughout the treatment stage. Pump P2 pumps regenerated dialysate out of the primary reservoir 304, into the fluid line 314, and into pump P2. While the regenerated dialysate exiting the sorbent cartridge 303 has been stripped of toxic substances that were absorbed from the patient's blood in the dialysis system 301, the regenerated dialysate must be further conditioned to meet acceptable physiological properties before being circulated back into the dialyzer 337 of the dialysis system 301 as fresh dialysate.

Accordingly, pump P4 continues to pump the electrolyte solution out of the bag 306 and into the fluid line 320, through ports (a) and (c) of valve V6, into an upper segment of the fluid line 319, through pump P4, and into the fluid line 314 at a flow rate that depends on (e.g., is a fraction of) the flow rate at which pump P2 pumps dialysate. Thus, pumps P2, P4 together form a closed pump control loop 332 that governs the flow rate at which pump P4 pumps the electrolyte solution, which is in a range of about 0.5 mL/min to about 5 mL/min. Furthermore, pump P3 continues to pump either the bicarbonate solution out of the bag 309 or the dilution water out of the bag 308, through port (c) of valve V5, into an upper segment of the fluid line 317, through pump P3, and into the fluid line 314 to further condition the dialysate.

As the dialysate passes through pump P2 and conductivity sensor CT1, the conductivity sensor CT1 detects a conductivity of the dialysate. Based on continuous measurements of the conductivity of the dialysate, either the bicarbonate solution or the dilution water will be continuously selected for addition to the dialysate through port (c) of valve V5, and the flow rate at which pump P3 pumps dialysate will be continuously adjusted to maintain a conductivity of the dialysate within a physiologically acceptable range of 13.5 mS/cm to 14.2 mS/cm. Generally, as a difference between the measured conductivity and an acceptable conductivity increases, the flow rate at which the pump P3 pumps fluid increases. Accordingly, as the difference between the measured conductivity and the acceptable conductivity decreases, the flow rate at which the pump P3 pumps fluid decreases. In this manner, the conductivity meter CT1 and the pump P3 together form a closed pump control loop 331 that regulates a flow rate at which the pump P3 pumps fluid. If the conductivity of the dialysate is too low during the first phase of the treatment stage, then bicarbonate solution is infused into the dialysate to raise the conductivity.

After passing the conductivity sensor CT1, the dialysate flows past the heat exchanger HX and temperature sensor T2. Based on a fluid temperature detected by temperature sensor T2, a power level of the heat exchanger HX will be adjusted to maintain the temperature of the dialysate at the set point temperature of the heat exchanger HX. In this way, temperature sensor T2 and heat exchanger HX form a closed heater control loop 333. The dialysate flows from the fluid line 315 through ports (c) and (b) of valve V2 into the fluid line 323 and past conductivity sensor CT2. As the dialysate passes conductivity sensor CT2, conductivity sensor CT2 performs a second check (e.g., downstream of heat exchanger HX) to detect a conductivity of the dialysate.

If the conductivity of the dialysate is outside of the acceptable range (e.g., either too low or too high), but within a predetermined range (e.g., that is broader than the acceptable range), then a safety system in electrical communication with the conductivity sensor will adjust a flow rate of infusion of the bicarbonate solution or the dilution water to achieve a conductivity within the acceptable range. If the conductivity level of the dialysate is outside of the predetermined physiologically safe range, then, in some implementations, the fluid conditioning system 100 will attempt to restore the safe fluid parameters and continue the treatment. For example, valves V3 and V4 will adjust to direct fluid through the bypass fluid line 336 and close fluid lines 324, 325 until a time at which the conductivity has again stably reached a physiologically safe range, at which time valves V3, V4 will adjust to close the bypass fluid line 336 and direct fluid to and from the dialysis system 301 via fluid lines 324, 325. In some implementations, a user may also be instructed to check that fluid levels of the bicarbonate solution and the dilution water are non-zero upon return of the conductivity to a physiologically safe range.

Over time, the sorbent cartridge 303 changes a composition of the regenerated dialysate exiting the sorbent cartridge 303 during the first phase of the treatment stage (e.g., an early, initial phase in which the patient's blood is initially circulated through the dialysis machine 301). For example, during the first phase of the treatment stage, levels of toxic substances within the spent dialysate are relatively high. The sorbent cartridge 303 converts urea into ammonium and captures the ammonium within one or more filtration layers within the sorbent cartridge 303 to remove the ammonium from the dialysate. While the filtration layers capture the ammonium, the filtration layers release sodium cations and other cations into the dialysate via cation exchange, which increases the conductivity and/or decreases the pH of the regenerated dialysate exiting the cartridge 303.

Over the course of the first phase of the treatment stage, spent dialysate entering the sorbent cartridge 303 contains fewer toxic substances (e.g., as uremic toxins are removed from the patient's blood), and the sorbent cartridge 303 releases more sodium cations. Therefore, the conductivity of the dialysate exiting the sorbent cartridge 303 gradually increases over time. Once the conductivity of the dialysate reaches a predetermined value in a range of about 13.8 mS/cm to about 14.0 mS/cm, the first phase of the treatment stage in which bicarbonate is used to regulate the conductivity of the dialysate concludes, and the second phase of the treatment stage begins.

During the second (e.g., later, final) phase of the treatment stage, bicarbonate is no longer used to regulate (e.g., increase) the conductivity of the dialysate, and dilution water is the sole substance at valve V5 that is used to regulate (e.g., decrease) the conductivity of the dialysate until the end of the treatment stage (e.g., the end of the second phase). Accordingly, port (b) of valve V5 is closed, while port (a) of valve V5 is opened. If the conductivity of the dialysate is too high during the second phase of the treatment stage, then dilution water is infused into the dialysate to lower the conductivity of the dialysate.

Over the course of the second phase of the treatment stage, an amount of ammonium captured in the sorbent cartridge 303 increases, such that a capacity of the sorbent cartridge 303 to absorb additional ammonium gradually decreases, and a level of ammonia within the regenerated dialysate eventually increases, once the capacity of the sorbent to adsorb ammonium is exhausted. The ammonia sensor NH detects the level of ammonia within the regenerated dialysate at a location downstream of the sorbent cartridge 303.

The treatment stage (e.g., including both the first and second phases) typically lasts a duration of about 120 min to about 300 min. For example, 240 minutes (e.g., 4 hours) is a standard duration that typically achieves adequate treatment for the vast majority of patients. Furthermore, most treatment stages will end after four hours without reaching the threshold ammonium concentration of 2 mg/dL (e.g., without ever approaching exhaustion of the filtering capabilities of the sorbent cartridge 303). The fluid conditioning system 100 will sound an audio alert signifying that the treatment completed successfully and that the patient can disconnect himself or herself from the dialyzer 337. However, if the ammonium level in the dialysate (e.g., as detected by the ammonia sensor NH) indicates that the sorbent cartridge 303 is no longer absorbing enough ammonium from the spent dialysate to maintain the ammonium level at or below an acceptable value of about 2 mg/dL prior to the standard treatment duration, then the treatment stage will conclude prematurely. Such conditions may occur occasionally for larger patients that have very high blood urea nitrogen (BUN) levels.

Throughout the fluid conditioning cycle, pressure transducers PT1, PT2, PT3, PT4 detect fluid pressures to regulate pump flow rates. For example, during all stages (e.g., the priming, infusion, and treatment stages) of the fluid conditioning cycle, pressure transducer PT1 forms a closed pump control loop 328 with pump P1 by detecting a fluid pressure of the dialysate within the fluid line 312 (e.g., located downstream of pump P1) and providing a feedback signal to pump P1 indicative of the fluid pressure. Based on the fluid pressure of the dialysate, an angular speed (e.g., an RPM level) of pump P1 is adjusted to maintain the flow rate within a desired range. During the treatment stage of the fluid conditioning cycle, pressure transducer PT4 forms an additional closed pump control loop 329 with pump P1 by detecting a fluid pressure of the dialysate exiting the dialysis system 301 (e.g., upstream of pump P1) and providing a forward signal to pump P1 indicative of the fluid pressure. Based on the fluid pressure of the dialysate, the angular speed of pump P1 is adjusted to closely match the flow rate at pump P1 with that of the dialysate exiting the dialysis system 301. Accordingly, the fluid pressure of the dialysate within the fluid line 312 (e.g., downstream of pump P1) is at least in part affected by the fluid pressure of the dialysate exiting the dialysis system 301 (e.g., upstream of pump P1).

Similarly, during all stages (e.g., the priming, infusion, and treatment stages) of the fluid conditioning cycle, pressure transducer PT2 forms a closed pump control loop 330 with pump P2 by detecting a fluid pressure of the dialysate within the fluid line 315 (e.g., located downstream of pump P2) and providing a feedback signal to pump P2 indicative of the fluid pressure. Based on the fluid pressure of the dialysate, an angular speed of pump P2 is adjusted to maintain the flow rate within a desired range. During the treatment stage of the fluid conditioning cycle, the flow rate at which pump P3 pumps fluid is regulated by a feedback signal from conductivity meter CT1 to form the pump control loop 331, and the flow rate at which pump P4 pumps the electrolyte solution is regulated by a feedback signal from pump P2 to form the pump control loop 332, as discussed above.

During all stages of the fluid conditioning cycle, pressure transducers PT3 and PT4 detect operation of the dialyzer 337. If measurements at pressure transducers PT3 and PT4 indicate that there is no fluid flow through the dialyzer 337, then the fluid conditioning system 100 will enter the bypass mode to flow dialysate through fluid line 336 and to avoid delivering dialysate to the dialysis system 301 via fluid lines 324, 325.

Figure 21:
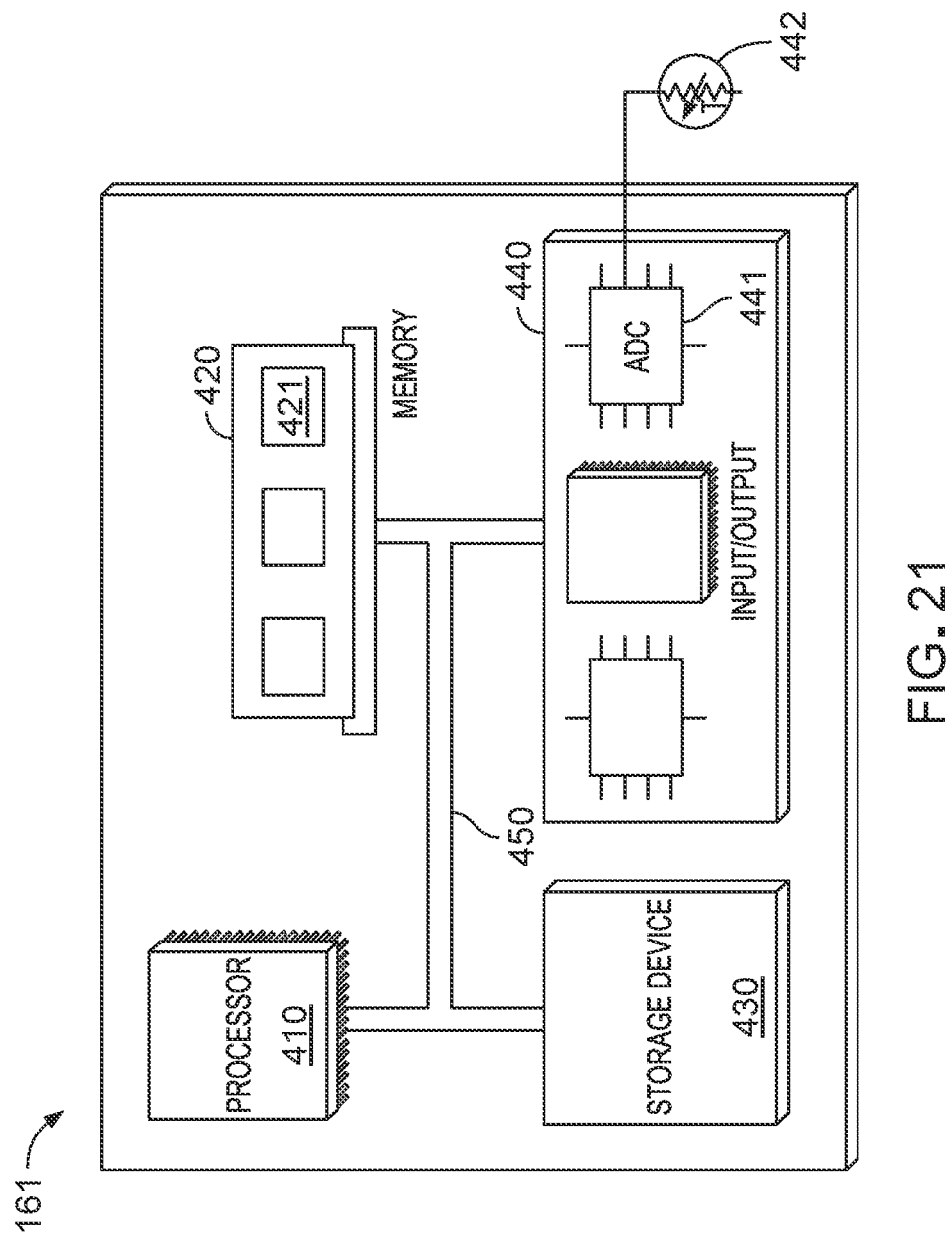
FIG. 21 provides a block diagram of a control system of the fluid conditioning system of FIG. 1.

FIG. 21 provides a block diagram of the control system 161. The control system 161 includes a processor 410, a memory 420, a storage device 430, and an input/output interface 440. In some embodiments, the control system 161 includes more than one processor 410, memory 420, storage device 430, and/or input/output interface 440. Each of the components 410, 420, 430, and 440 can be interconnected, for example, using a system bus 450. The processor 410 is capable of processing instructions for execution within the control system 161. The processor 410 can be a single-threaded processor, a multi-threaded processor, or a quantum computer. The processor 410 is capable of processing instructions stored in the memory 420 or on the storage device 430.

The memory 420 stores information within the control system 161. In some implementations, the memory 420 is a computer-readable medium. The memory 420 can, for example, be a volatile memory unit or a non-volatile memory unit. The storage device 430 is capable of providing mass storage for the control system 161. In some implementations, the storage device 430 is a non-transitory computer-readable medium. The storage device 430 can include, for example, a hard disk device, an optical disk device, a solid-state drive, a flash drive, magnetic tape, or some other large capacity storage device. The storage device 430 may alternatively be a cloud storage device, e.g., a logical storage device including multiple physical storage devices distributed on a network and accessed using a network.

The input/output interface 440 provides input/output operations for the control system 161. In some implementations, the input/output interface 440 includes one or more of network interface devices (e.g., an Ethernet card), a serial communication device (e.g., an RS-232 10 port), and/or a wireless interface device (e.g., an 802.11 card, a 3G wireless modem, or a 4G wireless modem). In some implementations, the input/output device includes driver devices configured to receive input data and send output data to other input/output devices, e.g., keyboard, printer and display devices (e.g., the display screen 148). In some implementations, mobile computing devices, mobile communication devices, and other devices are used.

In some implementations, the input/output interface 440 includes at least one analog-to-digital converter 441. An analog-to-digital converter converts analog signals to digital signals, e.g., digital signals suitable for processing by the processor 410. In some implementations, one or more sensing elements are in communication with the analog-to-digital converter 441, as will be discussed in more detail below.

In some implementations, the control system 161 is a microcontroller. A microcontroller is a device that contains multiple elements of a computer system in a single electronics package. For example, the single electronics package could contain the processor 410, the memory 420, the storage device 430, and input/output interfaces 440.

Figures 22, 23:
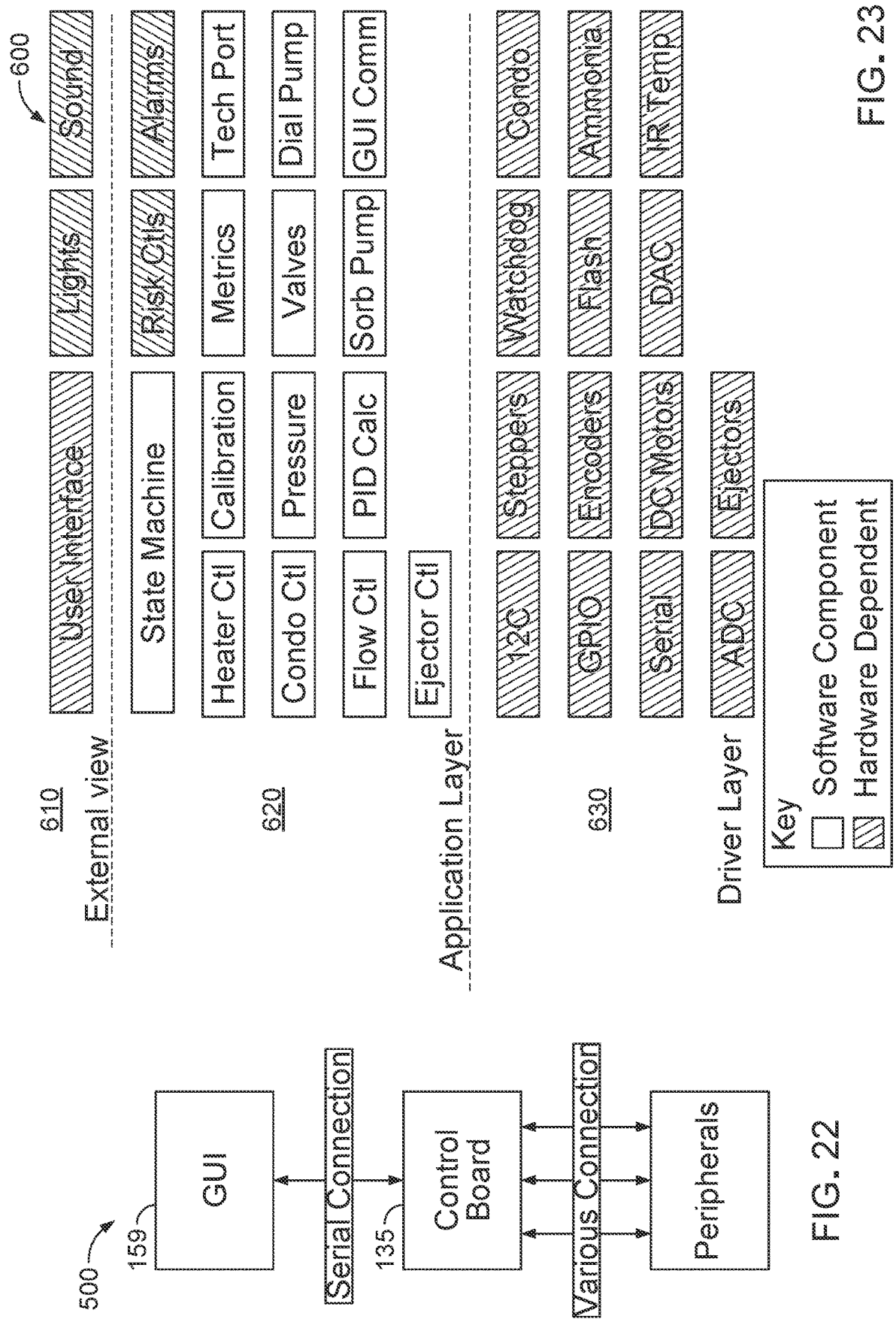
FIG. 22 provides a block diagram of a hardware system of the fluid conditioning system of FIG. 1.
FIG. 23 provides a block diagram of a software system of the fluid conditioning system of FIG. 1.

FIGS. 22 and 23 provide block diagrams of a hardware system 500 and a software system 600 of the fluid conditioning system 100 that are provided by the control system 161. As shown in FIG. 22, the hardware system 500 is provided by a circuit board for generating GUIs for display on the display screen 148 and one or more circuit boards 135 for controlling the electromechanical peripheral components of the fluid conditioning system 100, and the various electromechanical peripheral components. The software system 600 can be broken down into an external view 610, an application layer 620, and a driver layer 630. The external view 610 includes user interfaces provided by the GUIs, lights, sounds, and debug ports. The application layer 620 includes business logic, and the driver layer 630 is configured to implement peripheral-specific code (e.g., communication protocols and stepper motor drivers).

Once the treatment stage concludes, the fluid conditioning system 100 will drain the fluid circuit 350 of spent dialysate and dispose of the spent dialysate as waste. There are several ways that the drainage can occur. In one embodiment, the fluid line from that provides spent dialysate to the dialysis system is disconnected. The end of that line is then connected to a drain line, and the other end of that line is clamped shut. The user opens the door on the dialyzer, and the cartridge begins to gravity drain. The system opens fluid paths to initiate its own drain through. Other options involve partially draining the system and allowing the user to remove bags still containing liquid.

Referring to FIGS. 24-27, various drain procedures are illustrated, including a gravity drain, an active drain followed by gravity drain, and a fast drain procedure.

Figure 24:
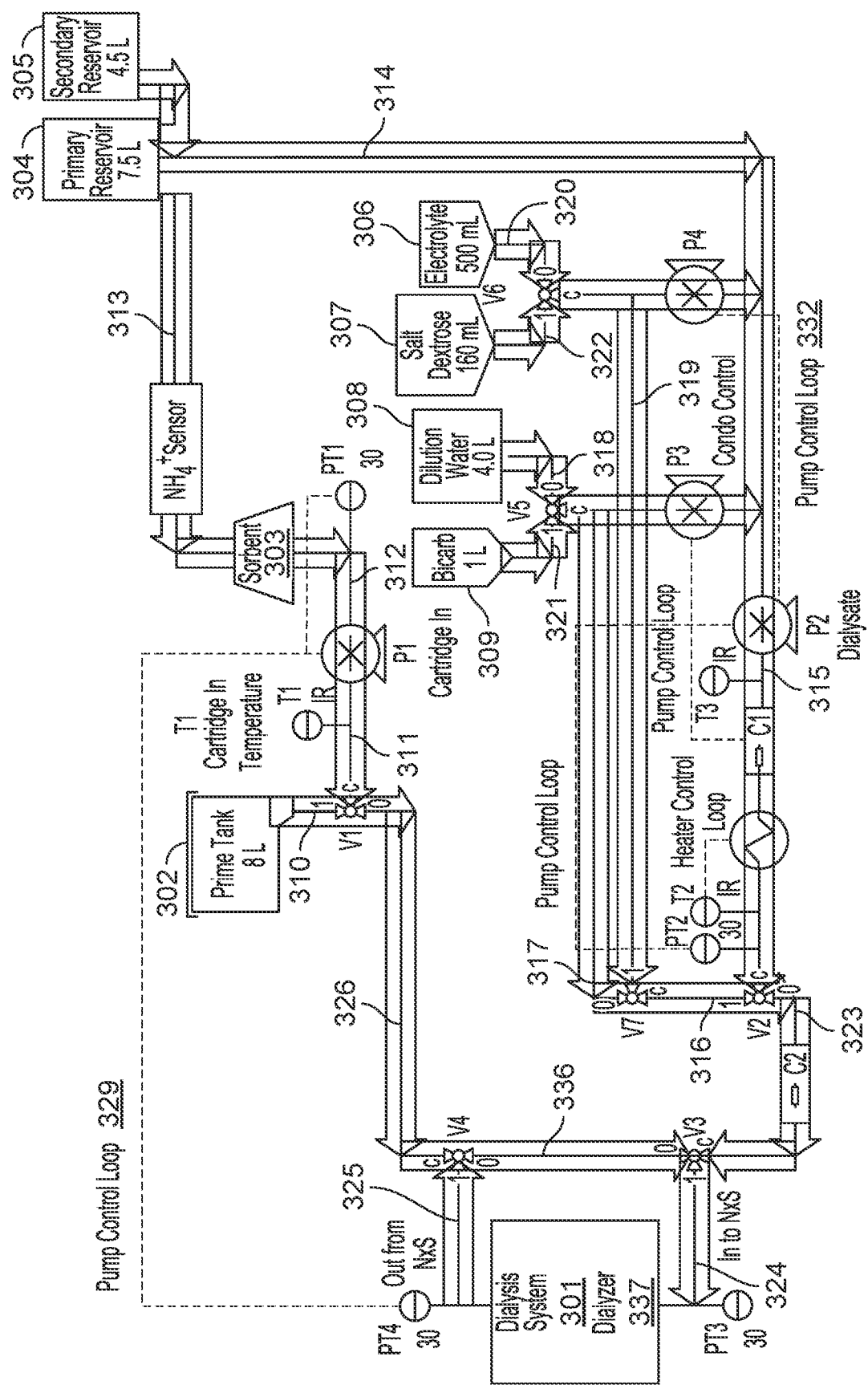
FIGS. 24-27 provide fluid flow paths of various drain schemes.

FIG. 24 shows a gravity drain. The dialysis system 301 is connected to drain as is typical for that system. The fluid line 325 bringing spent dialysate from the dialysis system 301 is no longer connected. However, the fluid line 324 taking fresh dialysate to the dialysis system 301 is still connected. All pumps are disengaged, and all valves are fully open in all three directions. The dialysis system 301 is also configured to gravity drain. As a variation of this procedure, either or both fluid lines 324, 325 may be directly connected to a drain line.

Figure 25:
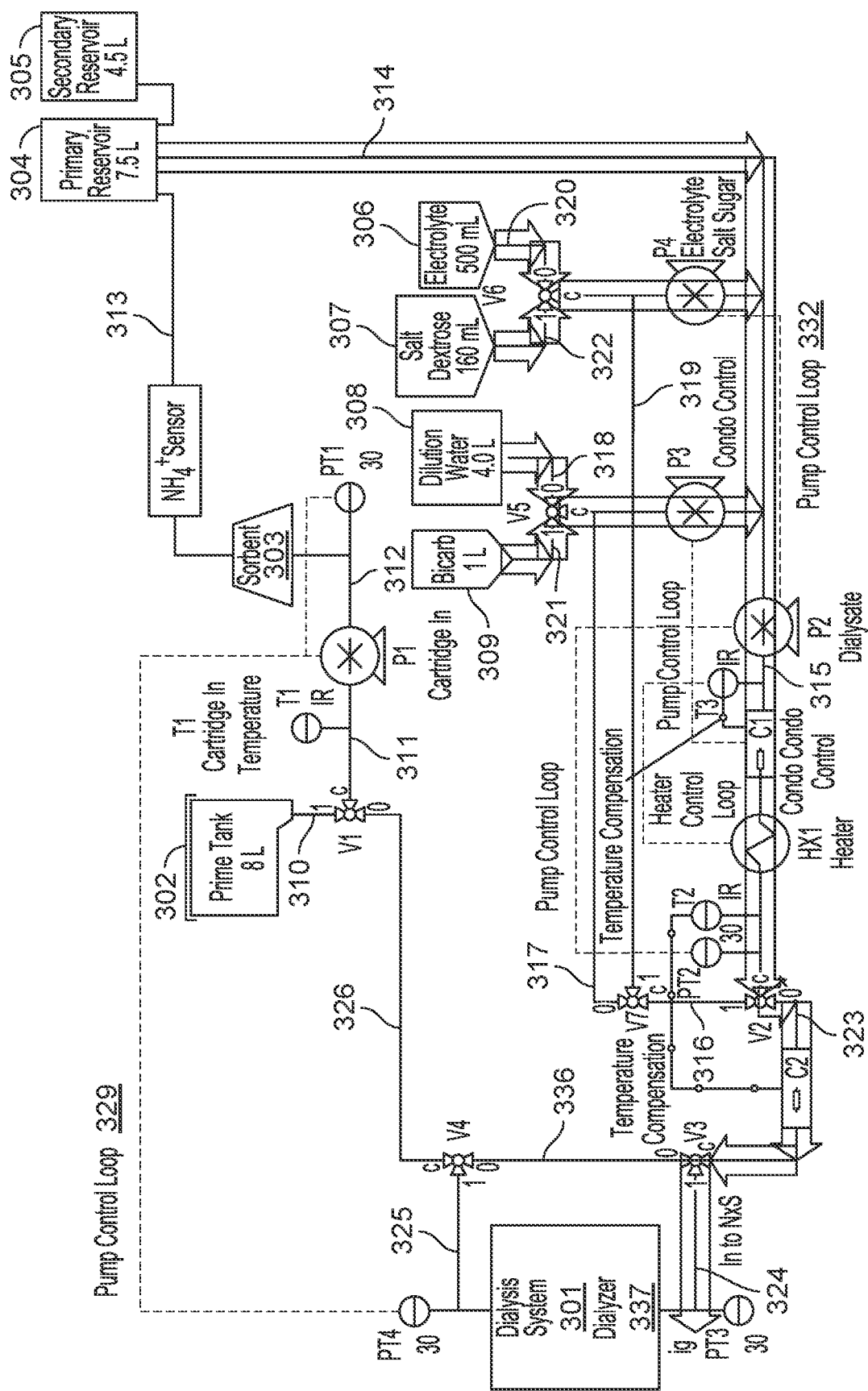

FIG. 25 shows the first step of the combined active drain/gravity drain procedure. The dialysis system 301 is connected to drain as is typical for that system. The fluid line 325 bringing spent dialysate from the dialysis system 301 is no longer connected. However, the fluid line 324 taking fresh dialysate to the dialysis system 301 is still connected. This step lasts for a maximum of 33 min, or until PT2 and PT3 sense a drop in pressure to near atmosphere, whichever comes first. As a variation of this procedure, the fluid line 324 may be connected directly to a drain line.

Figure 26:
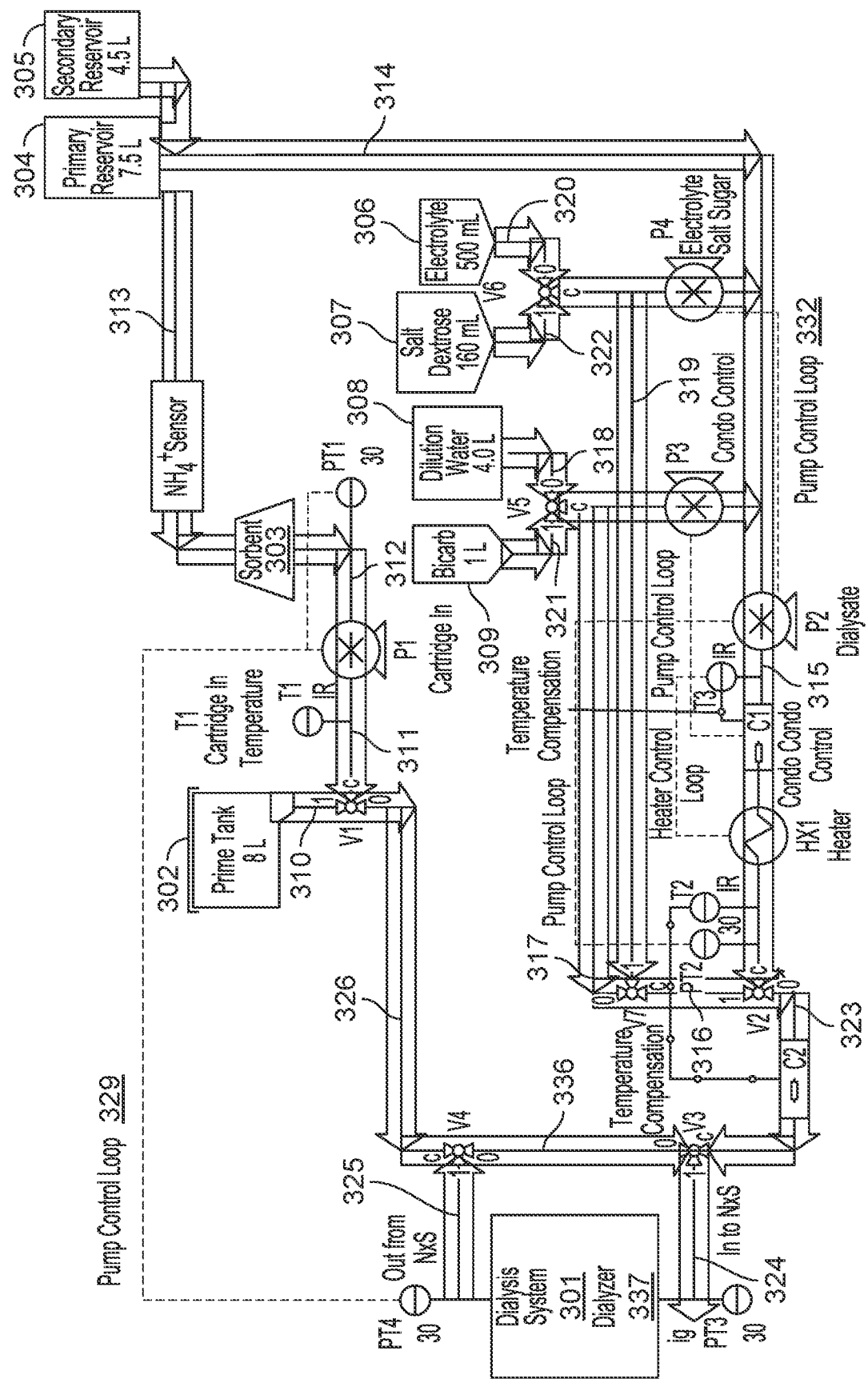

FIG. 26 shows the second step of the combined active drain/gravity drain procedure that allows the system to gravity drain any residual fluid, including fluid in the sorbent and prime tank. Three-way valves are positioned to open all ports. All pumps are disengaged to allow fluid to freely flow through the pump loops. As a variation of this step, one or both fluid lines 324, 325 may be connected to a drain line.

Figure 27:
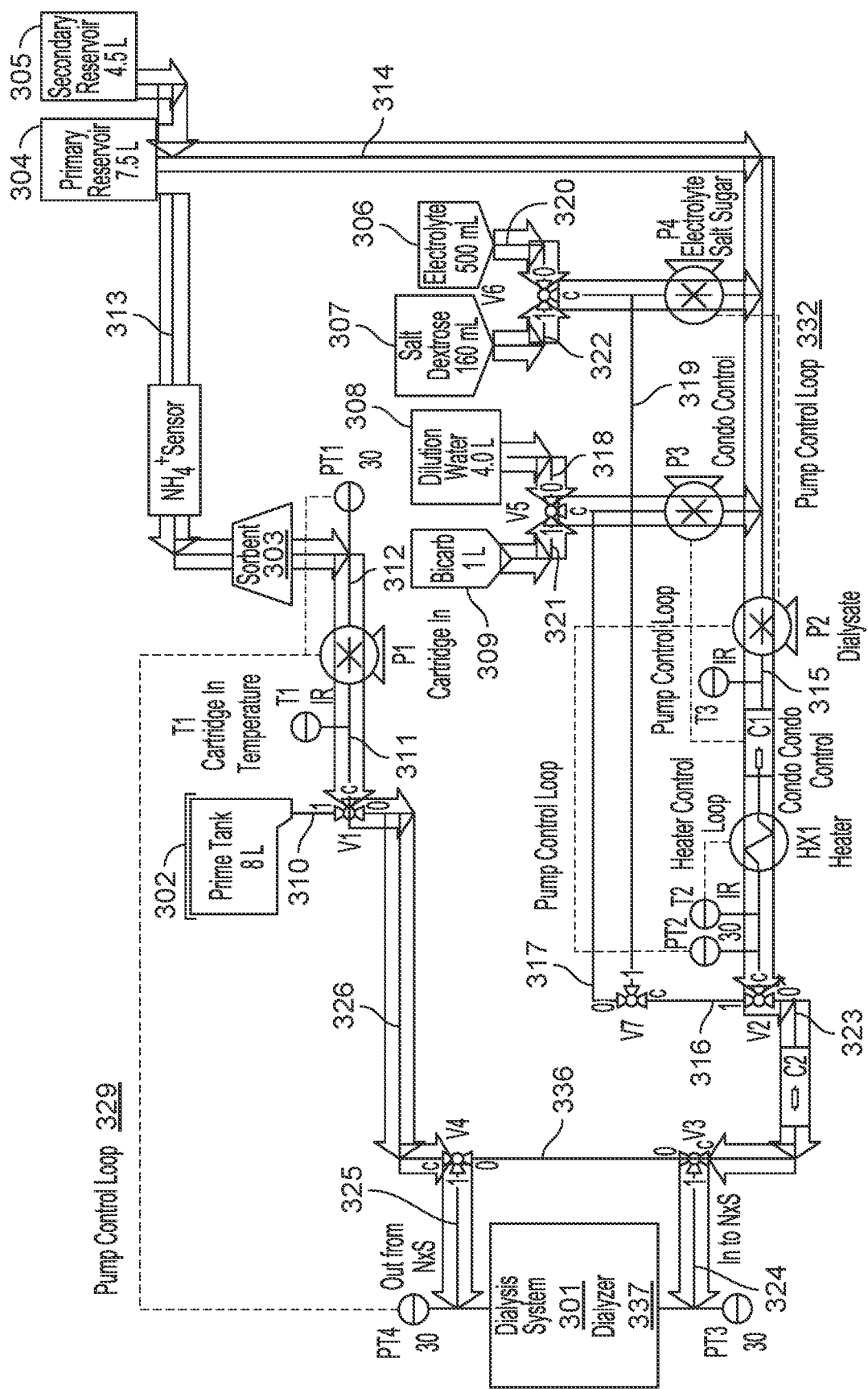

FIG. 27 shows the fast drain procedure. Both lines that would typically be connected to the dialysis system 301 are now each connected to drain lines. P1 flows in reverse at its maximum flow rate until the primary reservoir 304 is empty. Meanwhile, P2, P3, and P4 are also set to their maximum flow rates in the forward direction. First, valve V5 is set to drain BiCarb from bag 309, and valve V6 is set to drain electrolyte from bag 306. The salt/dextrose bag 307 is already empty, as it is designed to be completely used during the infusion step. Once the system decides that bag 309 is empty, valve V5 changes to empty dilution water from bag 308. The system is able to determine when the bags 309, 308, 306 are emptied through accounting of pump revolutions, by monitoring pressure, by monitoring conductivity, through the use of flow totalizers (not shown), and/or through user interaction. Once the system detects that all bags are drained, and the sorbent cartridge 303 is drained, the drain function is over. Some residual fluid may remain in lines.

Methods are described herein for regulating sodium content in the dialysate while using the system 100. In these methods, the sorbent cartridge 303 is used for filtering used dialysis solution in connection with a sodium control system in fluid communication with the sorbent cartridge 303 and conductivity sensors 203, which together regulate the sodium levels within the dialysis solution by controlling conductivity.

Previous sodium-control systems have used a dual-phase sodium regulation. This regulation is in accordance with a prescription guide, generally input by a user, which indicates what desired level of sodium concentration of the dialysate is desired, when averaged over the treatment. During the first treatment phase, a sodium chloride solution is added to the dialysate to regulate its conductivity. Typically, the amount of sodium chloride solution added to drive the relatively low level of sodium in the dialysate up to the prescription average concentration. The amount of sodium chloride added during a treatment can be significant. Then follows a second phase where the sodium concentration increases past the prescription average concentration. During this phase, the system compensates for the excess sodium present above the desired prescription amount by adding dilution water. The amount of dilution water added during a treatment can be significant. The sodium concentration in the dialysate over time thus fluctuates around the prescription average, as the system attempts to maintain the concentration at the prescription average at all times.

Figure 28:
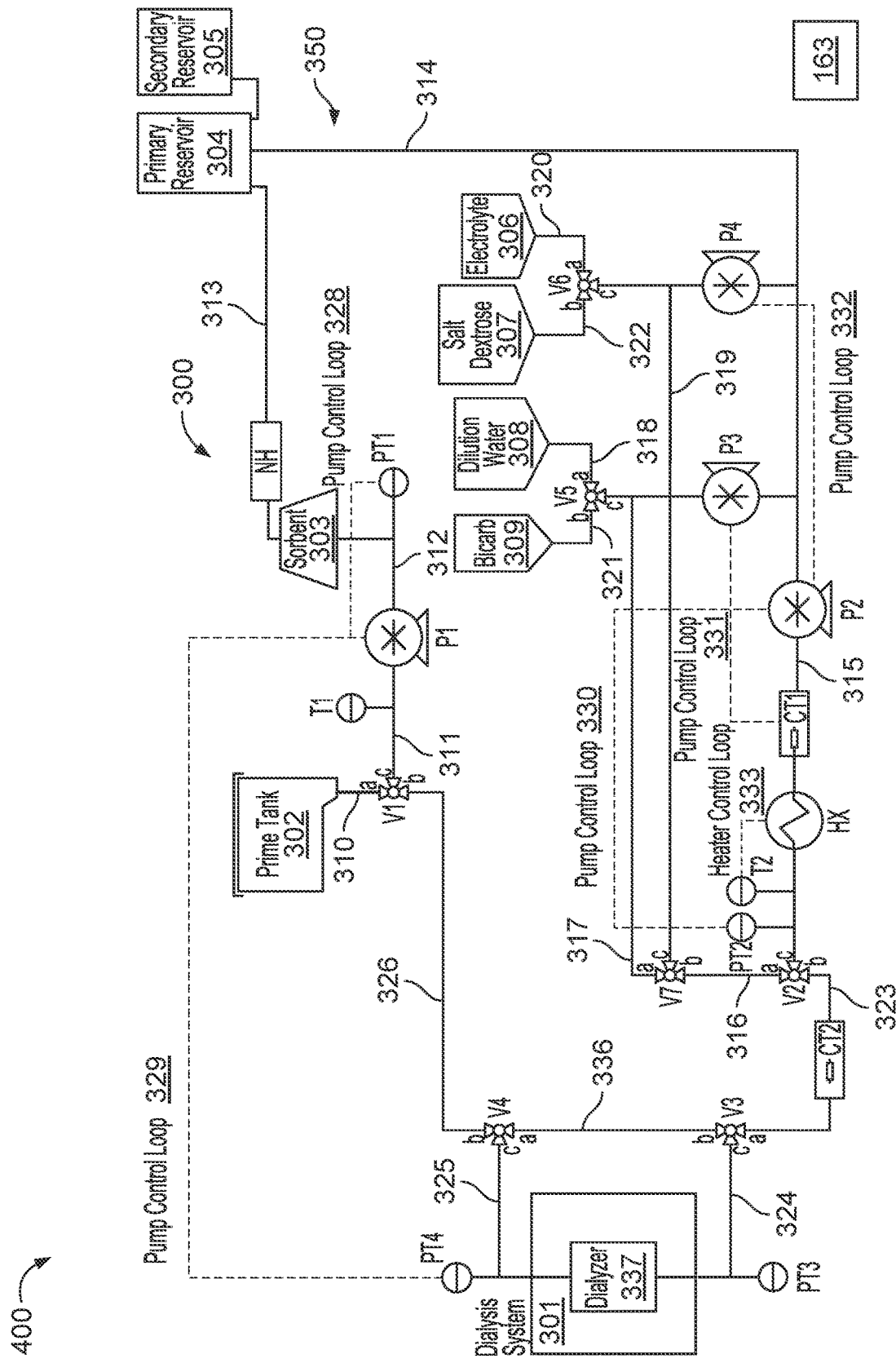
FIG. 28 illustrates a fluid flow path (indicated by highlighted bolded fluid lines) of a treatment stage of the fluid conditioning cycle carried out via the fluid circuit of FIG. 16.

Similar to FIG. 20 described above, the flow path arrangement 300 of FIG. 28 is operated as part of a fluid conditioning system 400 used with a sodium bicarbonate-based method of regulating sodium in the dialysate. The method used by the fluid conditioning system 400 ensures that the average sodium concentration of the dialysate for an overall treatment will be about equal to the desired prescription average concentration. The system 400 includes a sodium controller 163 that regulates the conductivity. The sodium control system 163 can be part of, or separate from the control system 161.

Figure 29:
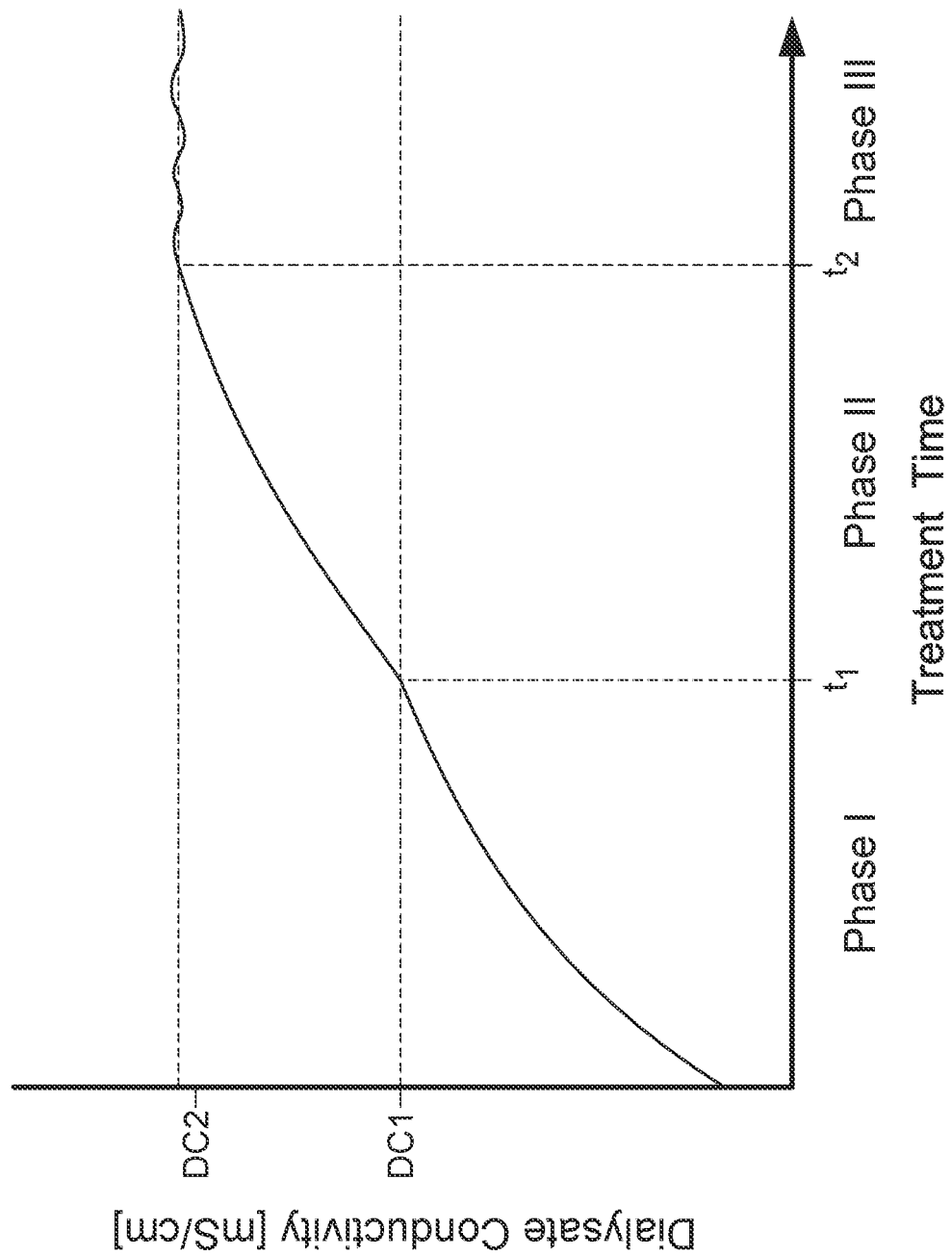
FIGS. 29-32 are graphs illustrating the dialysate concentration over a treatment duration for different exemplary patients.

Referring to FIG. 29, the sodium bicarbonate-based method of regulating sodium content used by system 400 sodium regulation has three phases. Similar to the first phase described above with respect to FIG. 20, during the first phase of the treatment (e.g., the early phase in which the patient's blood is initially circulated through the dialysis machine 301) the sorbent cartridge 303 changes the composition of the regenerated dialysate entering the sorbent cartridge 303. As the conductivity of the dialysate is too low during the phase I of the treatment stage (e.g., far below the prescription value) bicarbonate solution in the form of sodium bicarbonate contained in the bag 309 for containing a BC solution is infused into the dialysate.

During use, the sorbent cartridge 303 converts patient urea into ammonium and captures the ammonium within the filtration layers within the sorbent cartridge 303 to remove the ammonium from the dialysate. As the ammonium is captured, the filtration layers release sodium (and other cations) into the dialysate via cation exchange. This exchange depends on the concentration of cations in the dialysate entering the sorbent cartridge 303, as well as the properties of the sorbent cartridge 303. This exchange and the addition of BC solution increases the conductivity of the regenerated dialysate exiting the sorbent cartridge 303, as measured by the conductivity sensors 203 and shown in phase I.

As treatment progresses, the amount of ammonium that has been absorbed by the sorbent cartridge 303 and amount of sodium ions consequently released eventually results in a dialysate sodium concentration that is the prescribed average concentration. If left unchecked, the conductivity will continue to rise due to exchange caused by the patient's urea, even when BC solution is not added. Dilution water must be added at this stage.

The controller 163 of system 400 does not permit the dialysate conductivity to reach the prescribed value. Instead, the controller 163 directs the system 400 to stop adding sodium to the dialysate when the measured conductivity range is at a threshold dialysate conductivity value DC1. DC1 is lower than target desired prescription conductivity. For example, DC1 can be about 12.5 mS/cm. When DC1 is reached at time t1, the controller system 163 stops the influx of sodium bicarbonate. Phase I of the treatment stage concludes, and phase II begins.

During phase II, the conductivity of the dialysate continues to increase. However, this increase is due to the urea (or blood urea nitrogen or BUN) level of the patient, and not from the contents of the bag 309. Each patient has a native patient sodium concentration that varies across individuals. The sodium concentrations resulting in ion exchange across the dialyzer 337 and thus in the effluent exiting the sorbent cartridge 303 therefore has differing values for each patient. The sodium concentration in the dialysate exiting the sodium cartridge 303 during phase II is in effect customized to each patient, and his or her native urea level continues to drive the conductivity to the desired level. As a result, the conductivity continues to rise. The rising sodium concentration in dialysate is also a result of urea conversion in the sorbent. Patient urea crosses the dialyzer and enters the sorbent, which contains urease. Urease converts the urea to ammonia and CO2. The ammonia is then converted to ammonium, NH4+, and is captured by the zirconium phosphate (a cation exchanger) in the cartridge that exchanges the NH4+ for hydronium ions and sodium cations.

Phase II stops and phase III begins when the measured conductivity reaches the prescription value DC2. This conductivity prescription value DC2 is typically around 13.8 mS/cm. The prescription level can be altered slightly, from about 13.6 mS/cm to about 14.2 mS/cm. For example, the threshold concentration can be 13.6 mS/cm or 13.7 mS/cm, or can be 14.1 mS/cm or 14.2 mS/cm or more for a patient with a larger mass. As in phase II described above with respect to operation of the fluid conditioning system 100, during phase III for system 400 dilution water is infused into the circuit. From this time t2 dilution water is then used to regulate (e.g., decrease) the conductivity of the dialysate until the end of the treatment. As illustrated in FIG. 29, the dialysate conductivity can fluctuate somewhat around DC2.

In some examples, the system 400 can detect when the rate of change of the conductivity nears zero. A near-zero value (within a given tolerance) indicates that very little ion exchange is taking place, that is the value of the concentration slows as the final value is reached. The system 400 then starts phase III.

Advantageously, the bicarbonate-based sodium control method used by system 400 reduces the amount of total sodium added. The system 400 stops short of the desired final conductivity level and then lets the patient's own physiology drive the remaining increase in conductivity. In other modes of operation, sodium BiCarb can continue to be dosed to keep the dialysate conductivity higher. The exact choice of how the move from Phase I to II, or from II to III is triggered can depend on patient size, system features, and user preferences (e.g., the physician, technical, or patient). Tens of grams of sodium can be saved compared to adding sodium until the concentration reaches the desired level and then maintaining it at that level. There is less acidic sorbent, less sodium in the dialysate, and the system does not add more sodium than needed for a treatment. Consequently, less dilution water is needed during a treatment. For example, a maximum of 4.5 liters of dilution water is used. Advantageously, patient comfort is increased and the possibility of error reduced.

The system 400 uses a single prescription, and controls the volume of solution delivered based on conductivity. Individualized prescriptions are not necessary, e.g., prescriptions requiring solutions with differing amounts of powder in the supply bags 306, 307, 309 based on each patient's native BUN and prescription sodium concentration. Calculating and mixing of these solutions is not necessary, nor is a prescription guide for each patient. Instead, prior studies of the patient population allow the calculation of the maximum amount of powder that would be required for a treatment (e.g., driving to the threshold value, and a universal bag 309 can be used. A wide segment of the population can be treated with no system changes. Other benefits of the system 400 include reduced interaction needed from the patient and prescriber to carry out a treatment.

The sorbent cartridge 303 is designed such that the system 400 results in the desired final conductivity prescription. The resulting concentration of the dialysate is based on the amount of cation exchanger in the sorbent cartridge 303 when it is initially added to the flow path arrangement 300. For example, the sorbent cartridge 303 can include the following layers and materials: hydrous zirconium oxide-chloride (HZO-Cl), acetate, sodium zirconium carbonate or other alkali metal-Group IV metal-carbonate; zirconium phosphate or other ammonia adsorbents; alumina or other like material; alumina supported urease or other immobilized enzyme layer or other material to convert urea to ammonia, such as diatomaceous earth (or silica, ZSM-5, MM-22, etc.) or zirconium oxide; and granular activated carbon, such as charcoal, or other adsorbent. The sodium zirconium carbonate component acts as a phosphate adsorbent. The zirconium oxide can be capable of acting as a counter ion or ion exchanger to remove phosphate, and can be in the form of hydrous zirconium oxide (e.g., hydrous zirconium oxide containing acetate, or chloride).

Figure 30:
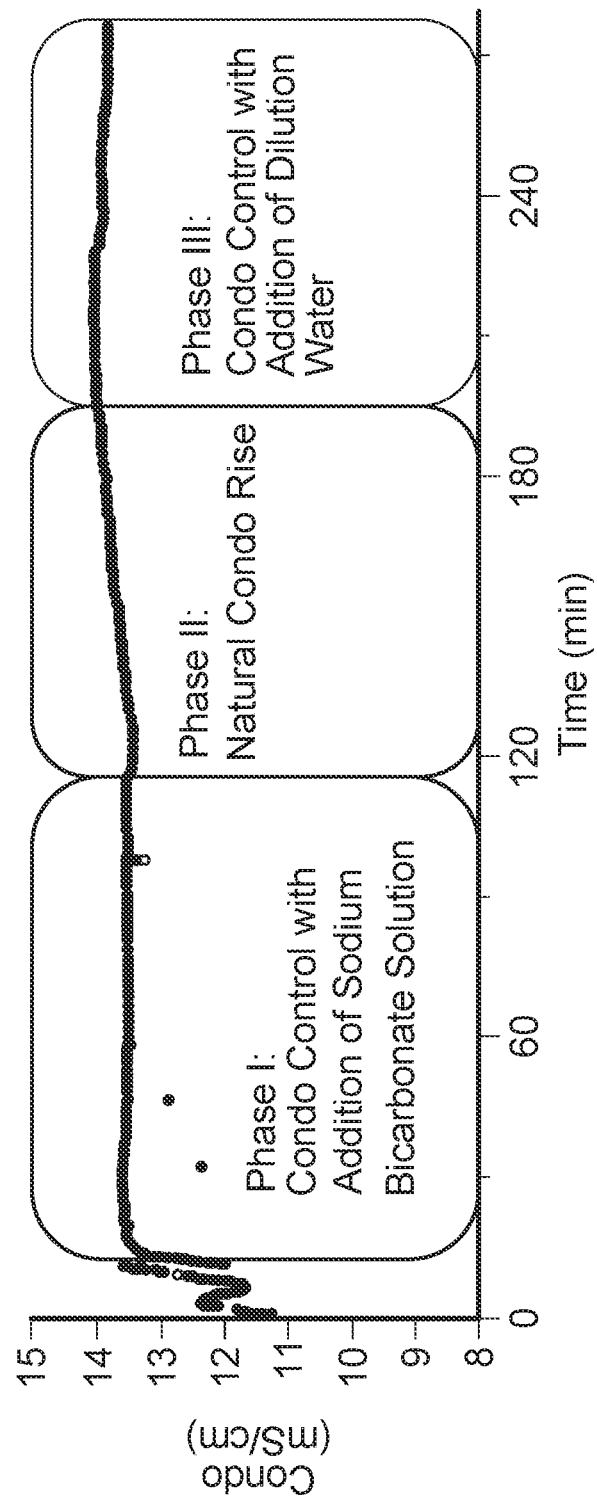

FIG. 30 is an example experiment showing dialysate conductivity during the treatment phase of with a simulated 20 L, 30 BUN patient. The different phases of treatment are highlighted. The initial oscillations (before Phase I) result from the infusion pattern used for this experiment. During this time, bicarbonate solution is being infused at 20 mL/min. During Phase I, conductivity is controlled at 13.5 mS/cm with addition of 0.6 M sodium bicarbonate. Once the fluid leaving the reservoir reaches a conductivity of 13.0 mS/cm, or equivalently, once dialysate conductivity reaches 13.5 mS/cm with little to no bicarb addition, then Phase I ends and Phase II begins. In Phase II, no adjustment is made to conductivity with either bicarb or dilution water. Once dialysate conductivity naturally rises to 14.0 mS/cm, Phase III begins. In Phase III, dilution water is infused into the dialysate stream to control dialysate conductivity. In this experiment, conductivity was controlled to 14.0 mS/cm for the first 30 minutes of Phase III; and then at 13.9 mS/cm for the next 30 min; and finally at 13.8 mS/cm for the remainder of treatment.

Figure 31:
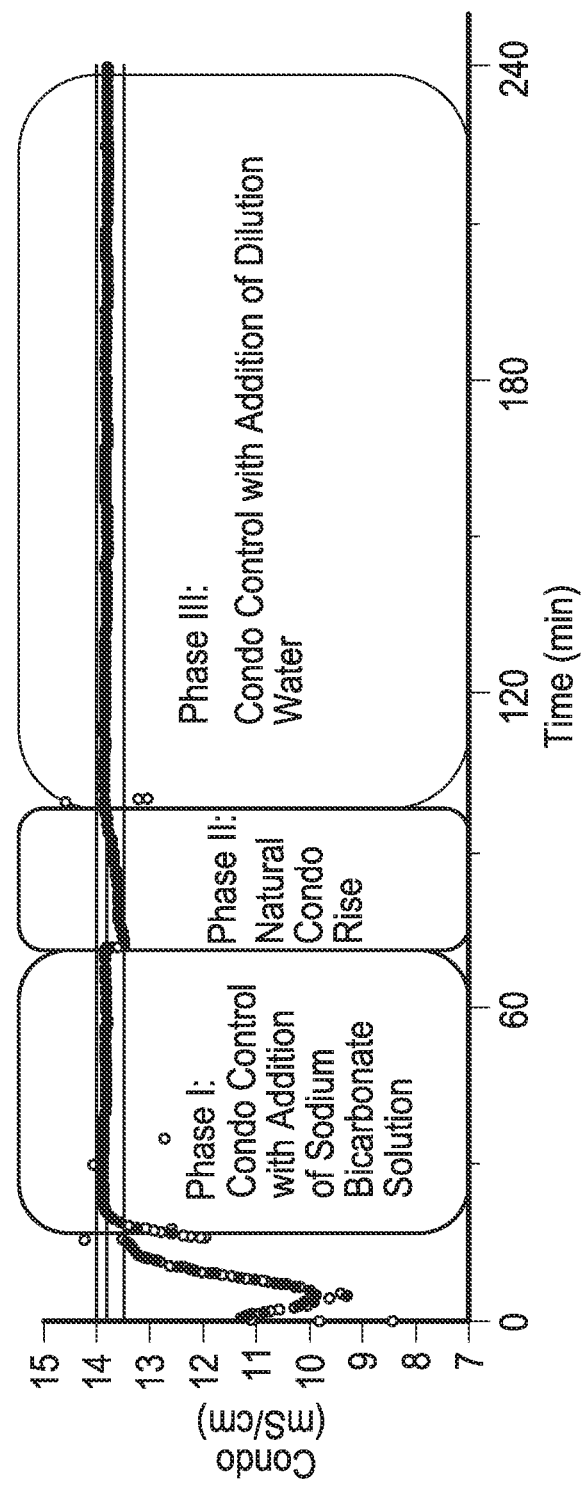

FIG. 31 is an example experiment showing dialysate conductivity during the treatment phase of with a simulated 40 L, 60 BUN patient (e.g., a larger patient than for the results shown in FIG. 30). The different phases of treatment are highlighted. The initial oscillations (before Phase I) result from the infusion pattern used for this experiment. During this time, bicarbonate solution is being infused at 20 mL/min. During Phase I, conductivity is controlled at 13.8 mS/cm with addition of 0.6 M sodium bicarbonate. Once the fluid leaving the reservoir reaches a conductivity of 13.0 mS/cm, or equivalently, once dialysate conductivity reaches 13.5 mS/cm with little to no bicarb addition, then Phase I ends and Phase II begins. In Phase II, no adjustment is made to conductivity with either bicarb or dilution water. Once dialysate conductivity naturally rises to 13.875 mS/cm, Phase III begins. In Phase III, dilution water is infused into the dialysate stream to control dialysate conductivity. In this experiment, conductivity was controlled to 13.8 mS/cm for the remainder of treatment.

Figure 32:
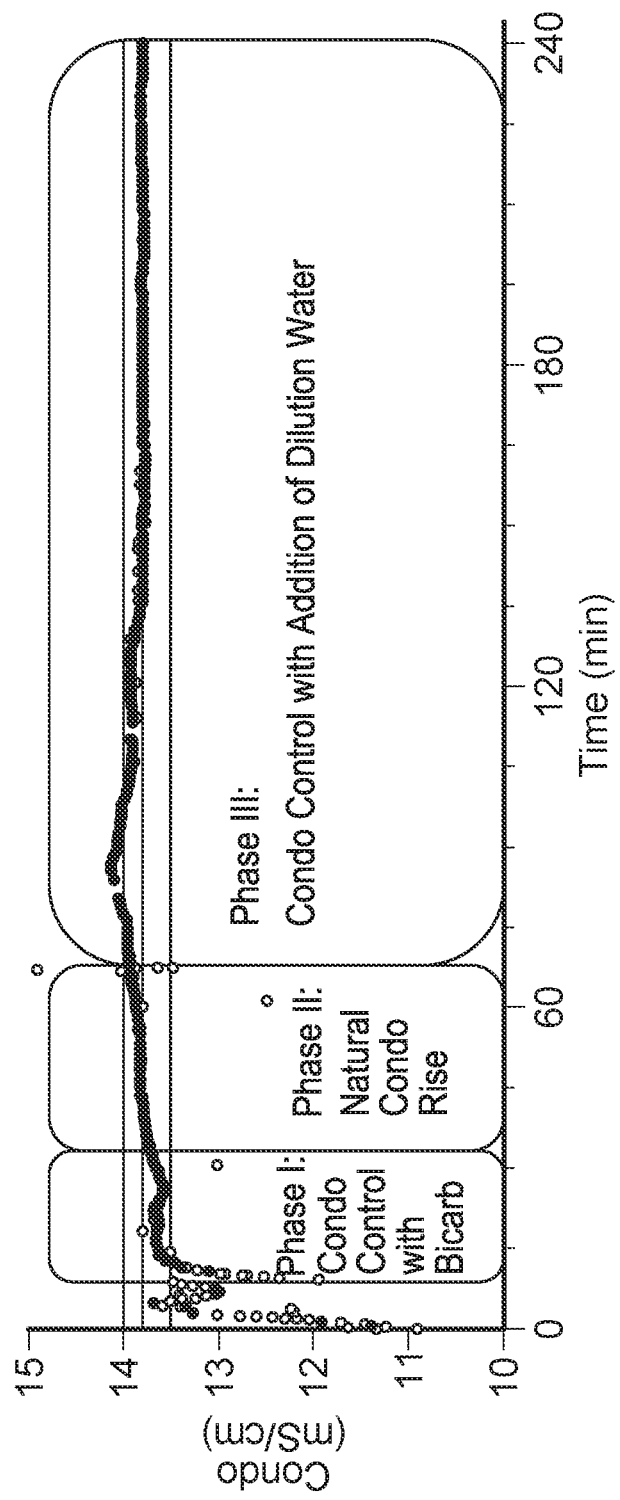

FIG. 32 is an example experiment showing dialysate conductivity during the treatment phase of with a simulated 60 L, 70 BUN patient (the largest patient of the examples shown). The different phases of treatment are highlighted. The initial oscillations (before Phase I) result from the infusion pattern used for this experiment. During this time, bicarbonate solution is being infused at 20 mL/min. During Phase I, conductivity is controlled to between 13.5 and 13.8 mS/cm with addition of 0.6 M sodium bicarbonate. Once the fluid leaving the reservoir reaches a conductivity of 13.3 mS/cm, or equivalently, once dialysate conductivity reaches 13.8 mS/cm with little to no bicarb addition, then Phase I ends and Phase II begins. In Phase II, no adjustment is made to conductivity with either bicarb or dilution water. Once dialysate conductivity naturally rises to 13.875 mS/cm, Phase III begins. In Phase III, dilution water is infused into the dialysate stream to control dialysate conductivity.

In this experiment, conductivity was controlled to 14.0 mS/cm for the first 30 minutes of Phase III; and then at 13.9 mS/cm for the next 30 min; and finally at 13.8 mS/cm for the remainder of treatment. This experiment shows a brief rise above 14.0 mS/cm within the first 30 minutes of Phase III, which resulted from a momentary suspension of dilution water infusion.

In some embodiments, the rate of change of the conductivity in the dialysate can determine when the system 400 moves to Phase II and to Phase III. In some embodiments, the transition point from phase I to II depends on the conductivity of the incoming fluid stream. Historically, a conductivity sensor that is post-reservoir but before the infusion point determined the transition point. Here, that conductivity measurement is not used for measurement, since that device no longer exists. Historically there have been phases: first with bicarb conductivity control; second with no infusion since already near the level desired; third being beyond desired level so add dilution water. Urea coming from patient to cartridge is converted to ammonia and adds sodium to the stream.

The conductivity sensor between reservoir 304, 305 and the infusion point (would be located on the fluid line 314) determines phase changes. If the conductivity sensor is not located there, the system cannot use sensor CT1 between the dialysate pump P2 and the heat exchanger HX1 since CT1 is a conductivity control sensor that is already being used. In normal conditions, sensor CT1 is measuring the set point or thereabouts.

Sensor CT1 is not used for determining out transition points. Instead, the response of the control system is used to determine transitions by indirectly using a conductivity meter as a readout device (as well as for control) and using response of the meter to the measurement. When the system is close to end of Phase I, due to the nature of the control loop the bicarb pump P3 slows down. When beginning Phase I, the bicarb dose is at 40 ml/min. When nearing the end of Phase I, dosing is at lower rate to maintain the same conductivity, approximately 1 ml/min or close to 0 or 5 ml/min. At DC1 slope is quite close to zero. After the reservoirs 304, 305 and before infusion (along fluid line 314), that curve has increasing dialysate conductivity with time throughout treatment. Bicarb solution is dosed in response to the difference between 13.8 mS/cm (or other desired dose) at t1, and the value before the infusion point and after the reservoir.

In some embodiments, the treatment begins with a low incoming concentration (e.g., below 13.3 mS/cm or 12.5 mS/cm) and gains conductivity at a set amount throughout treatment by dosing from pump 4, and dosing in response to the difference to 13.8 mS/cm, which determines concentration added by pump 3, in phase I. In Phase II, bicarb is no longer added. Incoming solution from the reservoirs 304, 305 is close to 13.3 mS/cm and additional of electrical solution is ~0.5 mS/cm. Without dilution or bicarb added it is around 13.8 mS/cm. As treatment continues, patient urea turns into sodium and increases conductivity beyond 13.3 mS/cm coming from reservoirs, and Phase III starts that is the opposite of Phase I. That is, it begins with a low rate of dilution water, and by end of the treatment the flow rate of dilution water has likely increased.

As there is no conductivity meter between the reservoirs and infusion port, the system can use the response of the control system to determine at a given moment the treatment is at which part of a phase. The control system will feedback loop to keep conductivity at CT1 to be 13.8 mS/cm. Transition from Phase I to II depends on activity of the P3 pump. If the increased flow rate being asked for is very small (near zero) then transition to Phase II. Once in Phase II, the conductivity control loop is reading conductivity, but that measurement is not controlling the pump. CT1 is solely a conductivity readout as it is not used as part of the loop. The conductivity of the system will still gradually rise; after reach the set threshold it will return to conductivity control process once again with CT1, switching valves for dilution water rather than bicarb, dependent on the difference to 13.8 mS/cm the system would otherwise be or how much above 13.3 mS/cm the fluid is before the electrolyte is infused but after the reservoir.

In this embodiment, during Phase III there is a plateau and the conductivity value post reservoir and pre-infusion continues to rise and thus progressively the increase amount of dilution water added. Thus the curve shown in FIG. 29 does not include the oscillation during Phase III. Additionally, the Y axis conductivity measurement refers to the value of the fluid pre-dialysate and post-reservoir before chemical dosing.

Non-limiting examples of urea-degrading enzymes that can be employed in either embodiment of the sorbent cartridge include enzymes that are naturally occurring (e.g. urease from jack beans, other seeds or bacteria), produced by recombinant technology (e.g., in bacterial, fungal, insect or mammalian cells that express and/or secrete urea-degrading enzymes) or produced synthetically (e.g., synthesized). In some embodiments, the enzyme is urease.

In certain embodiments, the sorbent cartridge 303 includes hollow fibers. The hollow fibers can reject positively charged ions, as well as increase the capacity of the cartridge. The hollow fibers can be coated with an ion-rejecting material, which through a water-purification like mechanism allows the urea through but rejects positively charged ions such as calcium and magnesium. The material coating the hollow fibers can be any such material known to one of skill in the art (e.g., fatty acids or polymer chains like polysulfone) that can effectively reject calcium and magnesium and therefore retain the ions in the dialysis solution. Alternatively, the hollow fibers can include an ion-selective nanofiltration membrane with pores sizes that prevent ionic substances from diffusing through the membrane.

A number of embodiments have been described in detail above. However, various modifications to these embodiments may be made without departing from the spirit and scope of the above disclosures. For example, while the fluid conditioning system 100 has been described and illustrated as including the pressure transducers 119 (PT1, PT2, PT3, PT4) for regulating pump flow rates, in some embodiments, a fluid conditioning system that is otherwise similar in construction and function to the fluid conditioning system 100 may alternatively include flow meters instead of pressure transducers for regulating pump flow rates. In some embodiments, a fluid conditioning system that is otherwise similar in construction and function to the fluid conditioning system 100 may not include pressure transducers or flow meters and may instead be RPM-controlled based on a detailed knowledge of the system operation to regulate pump flow rates.

While the fluid conditioning system 100 has been described and illustrated as including peristaltic pumps 103, 104 (P1, P2, P3, P4), in some embodiments, a fluid conditioning system that is otherwise similar in construction and function to the fluid conditioning system 100 may alternatively include a different type of pump, such as an impeller pump, a linear displacement pump, positive displacement pump, or a centrifugal pump.

While the fluid conditioning system 100 has been described and illustrated as including one overflow reservoir (e.g., the secondary reservoir 305), in some embodiments, a fluid conditioning system that is otherwise similar in construction and function to the fluid conditioning system 100 may include one or more additional overflow reservoirs. For example, in some embodiments, an additional reservoir may be connected to the fluid circuit 350 upstream of pump P1 or downstream of pump P2. In some embodiments, an additional reservoir may have a capacity different than that of either reservoir 304 or reservoir 305 or may have a zero volume capacity. In some embodiments, a reservoir may be permanently connected to a drain.

While the heater bag 153 has been described and illustrated as being arranged downstream of pump P2 of the fluid conditioning system 100, in some embodiments, a fluid conditioning system that is otherwise similar in construction and function to the fluid conditioning system 100 may include a heater bag or other heating element that is arranged at a different location along the fluid circuit 350 in order to achieve optimal temperature control of fluid flowing through the fluid circuit 350. For example, in some embodiments, a heater bag may be positioned immediately downstream of the sorbent cartridge 303 and may be powered based on signals from temperature sensor T1 to ensure that the temperature of the dialysis fluid is not high enough to damage internal components of the sorbent cartridge 303. In some embodiments, a heater bag may be located along the fluid circuit 350 anywhere between valve V1 and valve V2, as advantageous (e.g., to promote dissolution of the dry chemicals in the supply bags 306, 307, 309).

While the fluid conditioning system 100 has been described as including three-way valves V1-V7, in some embodiments, a fluid conditioning system that is otherwise similar in construction and function to the fluid conditioning system 100 may alternatively include one or more two-way valves to achieve the fluid flow path scenarios discussed above.

While an operation of the fluid conditioning system 100 has been described and illustrated with respect to certain flow rates, fluid volumes, temperatures, pressures, and time periods, in some embodiments, the fluid conditioning system 100 may be operated to carry out a fluid conditioning cycle with one or more different flow rates, fluid volumes, temperatures, pressures, and time periods, while still functioning to adequately condition dialysate for use in a cooperating dialysis system.

Although the example control system 161, the example hardware system 500, and the example software system 600 have been described respectively in FIGS. 21-23, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

Other embodiments are within the scope of the following claims.

What is claimed is:

1. A module configured to be connected to a dialysis machine having a dialyzer, the module being configured to remove one or more substances from a dialysis solution as the dialysis solution passes through the dialyzer, the module comprising:
a fluid line in fluid communication with the dialyzer;
a sorbent cartridge in fluid communication with the fluid line; and
a sodium control system in fluid communication with the fluid line, the sodium control system being adapted to actively alter a sodium concentration of the dialysis solution passing through the fluid line as the dialysis solution exits the sorbent cartridge; the sodium control system comprising:
  a conductivity sensor that is adapted to send a conductivity signal indicating a conductivity of the dialysis solution as the dialysis solution exits the sorbent cartridge, the conductivity sensor being in communication with the sodium control system, and
  a processor configured to receive the conductivity signal from the conductivity sensor, wherein the processor is configured to:
    compare the conductivity signal to a threshold value lower than a prescription value, and cause the sodium control system to stop actively altering the sodium concentration of the dialysis solution if the conductivity signal is greater than the threshold value but below the prescription value, and
    cause the sodium control system to add a diluent to the dialysis solution exiting the sorbent cartridge if the conductivity signal is greater than the prescription value.

2. The module according to claim 1, comprising a first container that stores sodium bicarbonate in communication with the fluid line.

3. The module according to claim 2, wherein the sodium control system is configured to introduce the sodium bicarbonate into the fluid line via a first pump.

4. The module according to claim 2, wherein actively altering the sodium concentration of the dialysis solution comprises introducing the sodium bicarbonate into the fluid line.

5. The module according to claim 1, comprising a second container that stores the diluent in communication with the fluid line.

6. The module according to claim 5, wherein the sodium control system is configured to introduce the diluent from the second container to the fluid line.

7. The module according to claim 6, wherein the sodium control system is configured to introduce the diluent to the fluid line when the processor indicates that the conductivity signal from the conductivity sensor is higher than the prescription value.

8. The module according to claim 1, wherein the sorbent cartridge comprises at least one layer of material capable of regenerating spent dialysis solution.

9. A dialysis system, comprising:
a dialysis machine comprising a dialyzer; and
a module that is connected to the dialysis machine, the module being configured to remove one or more substances from a dialysis solution as the dialysis solution passes through the dialyzer, the module comprising:
a fluid line in fluid communication with the dialyzer;
a sorbent cartridge in fluid communication with the fluid line; and
a sodium control system in fluid communication with the fluid line, the sodium control system being adapted to actively alter a sodium concentration of the dialysis solution passing through the fluid line as the dialysis solution exits the sorbent cartridge; the sodium control system comprising:
  a conductivity sensor that is adapted to send a conductivity signal indicating a conductivity of the dialysis solution as the dialysis solution exits the sorbent cartridge, the conductivity sensor being in communication with the sodium control system; and
  a processor configured to receive the conductivity signal from the conductivity sensor, wherein the processor is configured to:
    compare the conductivity signal to a threshold value lower than a prescription value, and cause the sodium control system to stop actively altering the sodium concentration of the dialysis solution if the conductivity signal is greater than the threshold value but below the prescription value, and
    cause the sodium control system to add a diluent to the dialysis solution exiting the sorbent cartridge if the conductivity signal is greater than the prescription value.

10. The dialysis system according to claim 9, wherein the dialysis machine is a hemodialysis machine.

11. The dialysis system according to claim 9, wherein the module comprises a first container that stores sodium bicarbonate in communication with the fluid line.

12. The dialysis system according to claim 11, wherein the sodium control system is configured to introduce the sodium bicarbonate into the fluid line via a first pump.

13. The dialysis system according to claim 11, wherein actively altering the sodium concentration of the dialysis solution comprises introducing the sodium bicarbonate into the fluid line.

14. The dialysis system according to claim 13, wherein the module comprises a second container that stores the diluent in fluid communication with the fluid line.

15. The dialysis system according to claim 14, wherein the sodium control system is configured to introduce the diluent from the second container to the fluid line.

16. The dialysis system according to claim 15, wherein the sodium control system is configured to introduce the diluent to the fluid line when the processor indicates that the conductivity signal from the conductivity sensor is higher than the prescription value.

17. The dialysis system according to claim 9, wherein the sorbent cartridge comprises at least one layer of material capable of regenerating spent dialysis solution.

18. A method, comprising:
removing one or more substances from spent dialysis solution by passing the spent dialysis solution through a sorbent cartridge;
receiving a conductivity signal from a conductivity sensor;
comparing the conductivity signal to a threshold value that is lower than a prescription value;
stopping altering a sodium concentration of the spent dialysis solution exiting the sorbent cartridge when the conductivity signal is greater than the threshold value but below the prescription value; and adding a diluent to the spent dialysis solution exiting the sorbent cartridge if the conductivity signal is greater than the prescription value.

19. The method according to claim 18, further comprising passing the spent dialysis solution exiting the sorbent cartridge through a dialysis machine.

* * * * *